[19] United States Patent
Lee et al.

(10) Patent No.: US 11,951,120 B2
(45) Date of Patent: Apr. 9, 2024

(54) MODIFICATION OF GENE TRANSCRIPTION AND TRANSLATION EFFICIENCY BY 5'UTR SEQUENCE VARIATION

(71) Applicant: Nanjing GeneLeap Biotechnology Co., Ltd., Nanjing (CN)

(72) Inventors: Jaewoo Lee, Cary, NC (US); Dehua Wang, Nanjing (CN); Xiaoyao Hao, Nanjing (CN); Yue Gao, Nanjing (CN); Jie Liu, Nanjing (CN); Shan He, Nanjing (CN); Ting He, Lexington, MA (US); Dan Tse, Andover, MA (US)

(73) Assignee: Nanjing GeneLeap Biotechnology Co., Ltd.

( * ) Notice: Subject to any disclaimer, the term of this patent is extended or adjusted under 35 U.S.C. 154(b) by 0 days.

(21) Appl. No.: 18/076,638

(22) Filed: Dec. 7, 2022

(65) Prior Publication Data
US 2023/0310484 A1 Oct. 5, 2023

Related U.S. Application Data

(60) Provisional application No. 63/287,484, filed on Dec. 8, 2021.

(51) Int. Cl.
*A61K 31/7105* (2006.01)
*A61K 38/00* (2006.01)
*C07K 14/025* (2006.01)
*C07K 14/54* (2006.01)

(52) U.S. Cl.
CPC ........ *A61K 31/7105* (2013.01); *C07K 14/025* (2013.01); *C07K 14/5434* (2013.01); *A61K 38/00* (2013.01)

(58) Field of Classification Search
None
See application file for complete search history.

(56) References Cited

FOREIGN PATENT DOCUMENTS

| WO | WO2013071047 | 5/2013 |
| WO | WO2017201350 | 11/2017 |
| WO | WO2018160540 | 9/2018 |

OTHER PUBLICATIONS

Carralot, J.-P. et al. 'Polarization of immunity induced by direct injection of naked sequence-stabilized mRNA vaccines.' CMLS Cellular and Molecular Life Sciences. vol. 61(Aug. 2004), pp. 2418-2424. (Year: 2004).*
Website URL: https//optimus5.cs.washington.edu (Year: 2019).*
Babendure, J.R. et al.'Control of mammalian translation by mRNA structure near caps.' RNA (Cambridge), vol. 12, No. 5 (2006), pp. 851-861. (Year: 2006).*
Sample, P.J. et al. 'Human 5'UTR design and variant effect prediction from a massively parallel translation assay.' Nature Biotechnology, vol. 37, No. 7 (Jul. 2019), pp. 803-809. (Year: 2019).*
Optimus 5-Prime Saturation Mutagenesis website: [https://optimus5.cs.washington.edu/MRL] (Year: 2019).*
Babendure et al., "Control of mammalian translation by mRNA structure near caps," RNA, May 2006, 12(5):851-861.
Conrad et al., "Maximizing transcription of nucleic acids with efficient T7 promoters," Communications Biol., Aug. 14, 2020, 3(1):439 (8 pages).
Etxeberria et al., "Intratumor Adoptive Transfer of IL-12 mRNA Transiently Engineered Antitumor CD8+T cells," Cancer Cell., Dec. 9, 2019, 36:613-629.
Hewitt et al., "Intratumoral IL12 mRNA Therapy Promotes TH1 Transformation of the Tumor Microenvironment," Clin Cancer Res., Dec. 1, 2020, 26(23):6284-6298.
NCBI GenBank Accession No. BC007075.1, "*Homo sapiens* hemoglobin, beta, mRNA (cDNA clone MGC:14540 IMAGE:4292125), complete cds," dated Sep. 23, 2014, 2 pages.
NCBI GenBank Accession No. MZ362873.1, "Synthetic construct clone WITO4160.27.ENV.gp145.G153E envelope glycoprotein gene, complete cds," dated Sep. 27, 2021, 2 pages.
NCBI GenBank Accession No. MK484107.1, "Firefly luciferase reporter vector pGL3c, complete sequence," dated Mar. 31, 2019, 3 pages.
NCBI Reference Sequence NM_000558.5, "*Homo sapiens* hemoglobin subunit alpha 1 (HBA1), mRNA," dated Nov. 8, 2021, 6 pages.
Sample et al., "Human 5' UTR design and variant effect prediction from a massively parallel translation assay," NatBiotech., Jul. 2019, 37(7):803-809.

* cited by examiner

*Primary Examiner* — Neil P Hammell
*Assistant Examiner* — Alexandra Geraldine Dace Denito
(74) *Attorney, Agent, or Firm* — Fish & Richardson P.C.

(57) ABSTRACT

This invention relates to the fields of mRNA vaccines, mRNA therapy, and gene therapy and specifically to the use of gene expression vectors or PCR amplicons containing various 5'UTR sequences followed by coding sequences for in vitro and in vivo production of mRNA or proteins of interest.

20 Claims, 5 Drawing Sheets

Specification includes a Sequence Listing.

MODIFICATION OF GENE TRANSCRIPTION AND TRANSLATION EFFICIENCY BY 5'UTR SEQUENCE VARIATION

CROSS-REFERENCE TO RELATED APPLICATIONS

This application claims the benefit of U.S. Provisional Application No. 63/287,484, filed on Dec. 8, 2021.

SEQUENCE LISTING

This application contains a Sequence Listing that has been submitted electronically as an XML file named Sequence.xml. The XML file, created on Nov. 17, 2022, is 97,308 bytes in size. The material in the XML file is hereby incorporated by reference in its entirety.

TECHNICAL FIELD

This invention relates to the fields of mRNA vaccines, mRNA therapy, and gene therapy and specifically to the use of gene expression vectors or PCR amplicons containing 5'UTR followed by coding sequences for in vitro and in vivo production of mRNA or proteins of interest.

BACKGROUND OF THE INVENTION mRNA vaccines, mRNA therapy, and gene therapy aim to treat or prevent various diseases using mRNA and genes encoding disease-specific proteins. In current mRNA vaccines and mRNA therapy, the mRNA is generated by in vitro transcription of genes encoding the target proteins and administered to patients. Then this mRNA is translated in vivo to the target proteins, which trigger host immune responses against, e.g., cancer cells and/or viruses, thereby leading to eradication of tumors and/or viruses, and/or prevention of tumor recurrence and/or virus infection/re-infection. On the other hand, gene therapy introduces target genes to patients. These target genes are transcribed and translated in vivo to produce target proteins. Thus, improvement of the efficiency of transcription and translation of genes encoding target proteins is a critical factor to improve the therapeutic effects of mRNA vaccines, mRNA therapy, and gene therapy, and to reduce the costs of mRNA vaccines and mRNA therapy.

5'UTR is a sequence upstream from the coding region of mRNA and a central regulator of translation of mRNA into protein. The 5'UTR is recognized by the ribosome which initiates the translation of mRNA. Each mRNA has a unique 5'UTR sequence to control mRNA translation. It has been shown that translation efficiency of mRNA is largely dependent on thermodynamic stability, location, and GC content of RNA structures in 5'UTR (Babendure J R et al. RNA. 2006. 12:851). No optimal 5'UTR structure, however, has yet been identified. Recent studies demonstrated that, using Optimus 5-Prime and a genetic algorithm, the relationship between 5'UTR sequences and translation efficiency could be predicted (Sample P J et al. Nat Biotech. 2019. 37:803). Using this model, we have designed new and optimal 5'UTR sequences for mRNA translation.

In addition to regulation of mRNA translation, 5'UTR might impact on gene transcription. Conrad et al used 5' rapid amplification of cDNA ends (RACE)-Seq to screen a randomized initially transcribed region of the T7 promoter. This study showed that the yield of mRNA transcribed in vitro from DNA templates using T7 bacteriophage polymerase varied depending on the specific 5'UTR sequences employed (Conrad T et al. Communications Biol. 2020. 3:439). These data led us to hypothesize that 5'UTR not only regulates translation of mRNA into proteins, but also regulates transcription of genes into mRNA.

No previous studies designed or screened optimal 5'UTR for both transcription and translation of genes from a DNA or RNA library. In this invention, we generated and compared various 5'UTR sequences of two different genes as to the efficiency of transcription and translation and found several novel 5'UTR sequences that have increased translation and/or transcription efficiency of these genes compared to known 5'UTR sequences. Our findings will significantly impact on mRNA vaccines, mRNA therapy, gene therapy, and mRNA manufacture.

SUMMARY OF THE INVENTION

In this invention, we designed over 70 different novel 5'UTR sequences with various lengths and secondary structures and high mean ribosome loading (MRL) prediction score calculated manually and by using the Optimus 5-Prime program. We demonstrated that different 5'UTR sequences differentially modulated the yield of mRNA in vitro transcribed from a plasmid encoding a reporter gene, a cytokine gene, or an HPV antigenic polypeptide coding sequence and the yield of proteins translated from mRNA encoding the same proteins. Furthermore, we observed that several novel 5'UTR sequences lead to higher transcription and/or translation efficiencies than known 5'UTR sequences, including the 5'UTR of Biontech's COVID vaccine mRNA BNT162b2, Moderna's COVID vaccine mRNA1273 (NCBI GenBank: MZ362873.1), human hemoglobin beta mRNA (HBB, NCBI GenBank: BC007075.1), and human hemoglobin alpha1 mRNA (HBA1, NCBI Sequence: NM_000558.5), while some 5'UTR sequences have significantly decreased translation and transcription efficiency compared to other 5'UTR sequences. These novel 5'UTR sequences could be used to improve or regulate the translation and/or transcription of mRNA and genes used in mRNA vaccines, mRNA therapy, and gene therapy.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings.

DETAILED DESCRIPTION OF THE INVENTION

Figure 1:
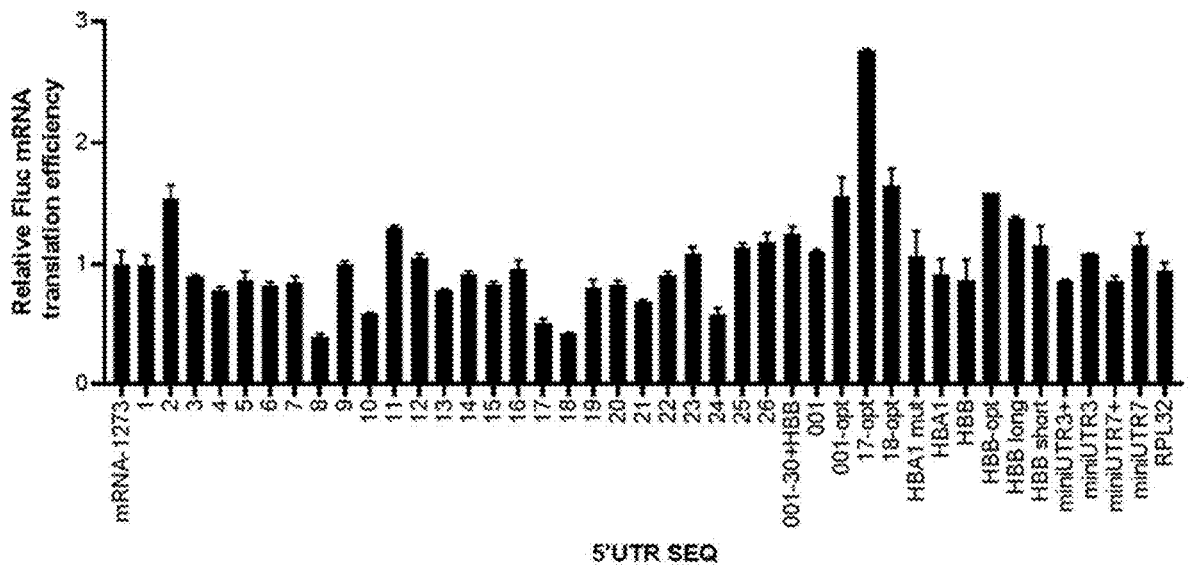
FIG. 1 Modulation of translational efficiency of FLuc gene by 5'UTR sequence optimization.

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa. As used herein and in the appended claims, the singular forms "a", "an", and "the" also refer to the plural forms unless the context clearly dictates otherwise.

In one aspect, the invention discloses an isolated nucleic acid comprising, in the 5' to 3' direction:
  a) at least one 5'UTR element, said 5'UTR element comprises polynucleotides comprising any one of SEQ ID NOs. 1-63, 72-84; and
  b) at least one open reading frame (ORF) encoding a peptide or protein of interest.

Preferably, the isolated nucleic acid of the present invention further comprises a 3'UTR element (such as a sequence comprising SEQ ID NO:87) and a polyA sequence.

In another aspect, said 5'UTR element comprises polynucleotides comprising any one of SEQ ID NOs. 38, 43, 46, 61 or 72.

In another aspect, said 5'UTR element consists of SEQ ID NOs. 38, 43, 46, 61 or 72.

In another aspect, said isolated nucleic acid sequence further comprises a 3'UTR element (such as a sequence comprising SEQ ID NO:87) and a polyA sequence.

In another aspect, said peptide or protein of interest is a pharmaceutically active protein, preferably selected from the group consisting of cytokines, such as interleukins (preferably IL-12, IL-2, or IL-7), erythropoietin; adhesion molecules, such as an integrin; immunoglobulins; immunologically active compounds, e.g., antigens, such as tumor-associated antigens, pathogen-associated antigens (e.g., one or more (e.g., 1, 2, 3, 4, 5, 6, 7, 8, 9, or 10) antigens of a virus, such as one or more (e.g., 1, 2, 3, 4, 5, 6, 7, 8, 9, or 10) antigens of human papillomavirus (HPV), Monkeypox virus, influenza virus (A, B, or C), CMV, or RSV), allergens, or autoantigens; hormones, such as vasopressin, insulin or growth hormone; growth factors, such as VEGFA; enzymes, such as herpes simplex virus type 1 thymidine kinase (HSV1-TK), hexosaminidase, phenylalanine hydroxylase, pseudo-cholinesterase, pancreatic enzymes, or lactase; receptors, such as growth factor receptors; protease inhibitors, such as alpha 1-antitrypsin; apoptosis regulators, such as BAX; transcription factors, such as FOXP3; tumor suppressor proteins, such as p53; structural proteins, such as surfactant proteins; reprogramming factors, such as OCT4, SOX2, c-MYC, KLF4, LIN28, or NANOG; genomic engineering proteins, such as clustered regularly spaced short palindromic repeat-CRISPR-associated protein 9 (CRISPR-Cas9); and blood proteins, such as fibrinogen.

Preferably, the cytokine is an interleukin, more preferably, said interleukin is IL-12, more preferably, said IL-12 is hIL-12, and most preferably, said hIL-12 coding sequence comprises SEQ ID NO:69 or SEQ ID NO:65.

Preferably, the HPV coding sequence comprises SEQ ID NO: 85.

In another aspect, the isolated nucleic acid comprises SEQ ID NO:68 or SEQ ID NO:86.

In an embodiment of the method of using the RNA or RNA composition of the invention, the method may comprise the step of transferring said RNA or RNA composition into a cell. In this respect, any technique which is suitable to transfer RNA into cells may be used. Preferably, the RNA is transfected into cells by standard techniques as described herein, e.g., calcium phosphate precipitation, DEAE transfection, electroporation, lipofection, or microinjection. The cell may be any cell which can be transfected with RNA and is preferably an antigen presenting cell, such as an immature antigen presenting cell, more preferably selected from the group consisting of macrophages, monocytes, B-cells, and dendritic cells. The method for producing a peptide or protein of interest may be performed in vivo or in vitro.

According to the invention, the term "cytokines" refers to proteins which have a molecular weight of about 1 to 200 kDa and which participate in cell signaling (e.g., paracrine, endocrine, and/or autocrine signaling). In particular, when released, cytokines exert an effect on the behavior of cells around the place of their release. Examples of cytokines include lymphokines, interleukins, chemokines, interferons, and tumor necrosis factors (TNFs). According to the present application, cytokines do not include hormones or growth factors. Cytokines differ from hormones in that (i) they usually act at much more variable concentrations than hormones and (ii) generally are made by a broad range of cells (nearly all nucleated cells can produce cytokines). Interferons are usually characterized by antiviral, antiproliferative and immunomodulatory activities. Interferons are proteins that alter and regulate the transcription of genes within a cell by binding to interferon receptors on the regulated cell's surface, thereby preventing viral replication within the cells. There are three types of IFNs that have distinctive biological activities. Type I IFNs include IFN-alpha, IFN-beta, and IFN-omega. Type II IFNs includes IFN-gamma. Type III IFNs include IFN-lambda 1, 2, 3, and 4. Particular examples of cytokines include erythropoietin (EPO), colony stimulating factor (CSF), granulocyte colony stimulating factor (G-CSF), granulocyte-macrophage colony stimulating factor (GM-CSF), tumor necrosis factor (TNF), bone morphogenetic protein (BMP), interferon alfa (IFNα), interferon beta (IFNβ), interferon gamma (INFγ), interleukin 2 (IL-2), interleukin 4 (IL-4), interleukin 10 (IL-10), interleukin 11 (IL-11), interleukin 12 (IL-12), interleukin 7 (IL-7), interleukin 15 (IL-15), interleukin 21 (IL-21), and interleukin 32 (IL-32).

According to the invention, the term "hormones" relates to a class of signaling molecules produced by glands, wherein signaling usually includes the following steps: (i) synthesis of a hormone in a particular tissue; (ii) storage and secretion; (iii) transport of the hormone to its target; (iv) binding of the hormone by a receptor; (v) relay and amplification of the signal; and (vi) breakdown of the hormone. Hormones differ from cytokines in that (1) hormones usually act in less variable concentrations and (2) generally are made by specific kinds of cells. Particular examples of hormones include insulin, vasopressin, prolactin, adrenocorticotropic hormone (ACTH), thyroid hormone, growth hormones (such as human grown hormone or bovine somatotropin), oxytocin, atrial-natriuretic peptide (ANP), glucagon, somatostatin, cholecystokinin, gastrin, leptins, catecholamines, gonadotropins, trophic hormones, and dopamine. In one embodiment, a "hormone" is a peptide or protein hormone, such as insulin, vasopressin, prolactin, adrenocorticotropic hormone (ACTH), thyroid hormone, growth hormones (such as human grown hormone or bovine somatotropin), oxytocin, atrial-natriuretic peptide (ANP), glucagon, somatostatin, cholecystokinin, gastrin, and leptins.

According to the invention, the term "adhesion molecules" relates to proteins which are located on the surface of a cell and which are involved in binding of the cell with other cells or with the extracellular matrix (ECM). Adhesion molecules are typically transmembrane receptors and can be classified as calcium-independent (e.g., integrins, immunoglobulin superfamily, lymphocyte homing receptors) and calcium-dependent (cadherins and selectins). Particular examples of adhesion molecules are integrins, lymphocyte homing receptors, selectins (e.g., P-selectin), and addressins.

Integrins are also involved in signal transduction. In particular, upon ligand binding, integrins modulate cell signaling pathways, e.g., pathways of transmembrane protein kinases such as receptor tyrosine kinases (RTK). Such regulation can lead to cellular growth, division, survival, or differentiation or to apoptosis. Particular examples of integrins include: $\alpha 1\beta 1$, $\alpha 2\beta 1$, $\alpha 3\beta 1$, $\alpha 4\beta 1$, $\alpha 5\beta 1$, $\alpha 6\beta 1$, $\alpha 7\beta 1$, $\alpha L\beta 2$, $\alpha M\beta 2$, $\alpha IIb3$, $\alpha V\beta 1$, $\alpha V\beta 3$, $\alpha V\beta 5$, $\alpha V\beta 6$, $\alpha V\beta 8$, and $\alpha 6\beta 4$.

According to the invention, the term "immunoglobulins" or "immunoglobulin superfamily" refers to molecules which are involved in the recognition, binding, and/or adhesion processes of cells. Molecules belonging to this superfamily share the feature that they contain a region known as immunoglobulin domain or fold. Members of the immunoglobulin superfamily include antibodies (e.g., IgA, IgD, IgE, IgG, and IgM), T cell receptors (TCRs), B cell receptors (BCRs), major histocompatibility complex (MHC) molecules, co-receptors (e.g., CD4, CD8, CD19), antigen receptor accessory molecules (e.g., CD-3γ, CD3-δ, CD-3ε, CD79a, CD79b), co-stimulatory or inhibitory molecules (e.g., CD28, CD80, CD86), and others (e.g., CD147, CD90, CD7).

According to the invention, the term "immunologically active compound" relates to any compound altering an immune response, preferably by inducing and/or suppressing the maturation of immune cells, inducing and/or suppressing cytokine biosynthesis, and/or altering humoral immunity by stimulating antibody production by B cells. Immunologically active compounds possess potent immunostimulatory activity including, but not limited to, antiviral and antitumor activity, and can also down-regulate other aspects of the immune response, for example, shifting the immune response away from a TH2 immune response, which is useful for treating a wide range of TH2 mediated diseases. Immunologically active compounds can be useful as vaccine adjuvants. Particular examples of immunologically active compounds include interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, selectins, homing receptors, and antigens, in particular tumor-associated antigens, pathogen-associated antigens (such as bacterial, parasitic, or viral antigens (such as one or more (e.g., 1, 2, 3, 4, 5, 6, 7, 8, 9, or 10) antigens of human papillomavirus (HPV), Monkeypox virus, influenza virus (A, B, or C), CMV or RSV)), allergens, and autoantigens.

According to the invention, the term "autoantigen" or "self-antigen" refers to an antigen which originates from within the body of a subject (i.e., the autoantigen can also be called "autologous antigen") and which produces an abnormally vigorous immune response against this normal part of the body. Such vigorous immune reactions against autoantigens may be the cause of "autoimmune diseases".

According to the invention, the term "allergen" refers to a kind of antigen which originates from outside the body of a subject (i.e., the allergen can also be called "heterologous antigen") and which produces an abnormally vigorous immune response in which the immune system of the subject fights off a perceived threat that would otherwise be harmless to the subject. "Allergies" are the diseases caused by such vigorous immune reactions against allergens. An allergen usually is an antigen which is able to stimulate a type-I hypersensitivity reaction in atopic individuals through immunoglobulin E (IgE) responses. Particular examples of allergens include allergens derived from peanut proteins (e.g., Ara h 2.02), ovalbumin, grass pollen proteins (e.g., Phl p 5), and proteins of dust mites (e.g., Der p 2).

According to the invention, the term "growth factors" refers to molecules which are able to stimulate cellular growth, proliferation, healing, and/or cellular differentiation. Typically, growth factors act as signaling molecules between cells. The term "growth factors" includes particular cytokines and hormones which bind to specific receptors on the surface of their target cells. Examples of growth factors include bone morphogenetic proteins (BMPs), fibroblast growth factors (FGFs), vascular endothelial growth factors (VEGFs), such as VEGFA, epidermal growth factor (EGF), insulin-like growth factor, ephrins, macrophage colony-stimulating factor, granulocyte colony-stimulating factor, granulocyte macrophage colony-stimulating factor, neuregulins, neurotrophins (e.g., brain-derived neurotrophic factor (BDNF), nerve growth factor (NGF)), placental growth factor (PGF), platelet-derived growth factor (PDGF), renalase (RNLS) (anti-apoptotic survival factor), T-cell growth factor (TCGF), thrombopoietin (TPO), transforming growth factors (transforming growth factor alpha (TGF-α), transforming growth factor beta (TGF-β)), and tumor necrosis factor-alpha (TNF-α). In one embodiment, a "growth factor" is a peptide or protein growth factor.

According to the invention, the term "enzymes" refers to macromolecular biological catalysts which accelerate chemical reactions. Like any catalyst, enzymes are not consumed in the reaction they catalyze and do not alter the equilibrium of the said reaction. Unlike many other catalysts, enzymes are much more specific. In one embodiment, an enzyme is essential for the homeostasis of a subject, e.g., any malfunction (in particular, decreased activity which may be caused by any of mutation, deletion or decreased production) of the enzyme results in a disease. Examples of enzymes include enzymes of the biosynthesis or degradation of cholesterol, steroidogenic enzymes, kinases, nucleases, phosphodiesterases, methylases, de-methylases, dehydrogenases, cellulases, proteases, lipases, phospholipases, aromatases, cytochromes, adenylate or guanylate cyclases, and neuramidases, such as tissue plasminogen activator, streptokinase, herpes simplex virus type 1 thymidine kinase (HSV1-TK), hexosaminidase, phenylalanine hydroxylase, pseudocholinesterase, pancreatic enzymes (e.g., amylase, lipase, and protease or mixtures thereof (such as pancrelipase)), and lactase.

According to the invention, the term "receptors" refers to protein molecules which receive signals (in particular chemical signals called ligands) from outside a cell. The binding of a signal (e.g., ligand) to a receptor causes some kind of response of the cell, e.g., the intracellular activation of a kinase. Receptors include transmembrane receptors (such as ion channel-linked (ionotropic) receptors, G protein-linked (metabotropic) receptors, and enzyme-linked receptors) and intracellular receptors (such as cytoplasmic receptors and nuclear receptors). Particular examples of receptors include steroid hormone receptors, growth factor receptors, and peptide receptors (i.e., receptors whose ligands are peptides), such as P-selectin glycoprotein ligand-1 (PSGL-1). The term "growth factor receptors" refers to receptors which bind to growth factors. Growth factor receptors are the first step of the signaling cascade for cell differentiation and proliferation. Growth factor receptors may use the JAK/STAT, MAP kinase, and/or PI3 kinase pathways.

According to the invention, the term "protease inhibitors" refers to molecules, in particular peptides or proteins, which inhibit the function of proteases. Protease inhibitors can be classified by the protease which is inhibited (e.g., aspartic protease inhibitors, cysteine protease inhibitors, metalloprotease inhibitors, serine protease inhibitors, threonine protease inhibitors, trypsin inhibitors) or by their mechanism of action (e.g., suicide inhibitors, such as serpins). Particular examples of protease inhibitors include serpins, such as alpha 1-antitrypsin, aprotinin, and bestatin.

According to the invention, the term "apoptosis regulators" refers to molecules, in particular peptides or proteins, which modulate apoptosis, i.e., which either activate or inhibit apoptosis. Apoptosis regulators can be grouped into two broad classes: those which modulate mitochondrial function and those which regulate caspases. The first class includes proteins (e.g., BCL-2, BCL-xL) which act to preserve mitochondrial integrity by preventing loss of mitochondrial membrane potential and/or release of proapoptotic proteins such as cytochrome C into the cytosol. The first class also includes proapoptotic proteins (e.g., BAX, BAK, BIM) which promote release of cytochrome C. The second class includes proteins such as the inhibitors of apoptosis proteins (e.g., XIAP) or FLIP which block the activation of caspases. Particular examples of apoptosis regulators are BAX, BCL-2, BCL-xL, BAK, BIM, XIAP, and FLIP, in particular BAX.

According to the invention, the term "transcription factors" relates to proteins which regulate the rate of transcription of genetic information from DNA to messenger RNA, in particular by binding to a specific DNA sequence. Transcription factors may regulate cell division, cell growth, and cell death throughout life;

cell migration and organization during embryonic development; and/or regulate transcription in response to signals from outside the cell, such as a hormone. Transcription factors contain at least one DNA-binding domain which binds to a specific DNA sequence, usually adjacent to the genes which are regulated by the transcription factors. Particular examples of transcription factors include hepatocyte nuclear factors, MECP2, insulin promoter factor 1, FOXP2, FOXP3, the STAT protein family, p53, the HOX protein family, and the SOX proteins, such as SOX2.

According to the invention, the term "tumor suppressor proteins" relates to molecules, in particular peptides or proteins, which protect a cell from one step on the path to cancer. Tumor-suppressor proteins (usually encoded by corresponding tumor-suppressor genes) exhibit a weakening or repressive effect on the regulation of the cell cycle and/or promote apoptosis. Their functions may be one or more of the following: repression of genes essential for the continuance of the cell cycle; coupling the cell cycle to DNA damage (as long as damaged DNA is present in a cell, no cell division should take place); initiation of apoptosis, if the damaged DNA cannot be repaired; metastasis suppression (e.g., preventing tumor cells from dispersing, blocking loss of contact inhibition, and inhibiting metastasis); and DNA repair. Particular examples of tumor-suppressor proteins include p53, phosphatase and tensin homolog (PTEN), SWI/SNF (SWItch/Sucrose Non-Fermentable), von Hippel-Lindau tumor suppressor (pVHL), adenomatous polyposis coli (APC), CD95, suppression of tumorigenicity 5 (ST5), suppression of tumorigenicity 14 (ST14), and Yippee-like 3 (YPEL3).

According to the invention, the term "structural proteins" refers to proteins which confer stiffness and rigidity to otherwise-fluid biological components. Structural proteins are mostly fibrous (such as collagen and elastin) but may also be globular (such as actin and tubulin). Usually, globular proteins are soluble as monomers, but polymerize to form long fibers which, for example, may make up the cytoskeleton. Other structural proteins are motor proteins (such as myosin, kinesin, and dynein) which are capable of generating mechanical forces, and surfactant proteins. Particular examples of structural proteins include collagen, fibroin, fibrinogen, surfactant protein A, surfactant protein B, surfactant protein C, surfactant protein D, elastin, tubulin, actin, and myosin.

According to the invention, the term "reprogramming factors" or "reprogramming transcription factors" relates to molecules, in particular peptides or proteins, which, when expressed in somatic cells optionally together with further agents such as further reprogramming factors, lead to reprogramming or de-differentiation of said somatic cells to cells having stem cell characteristics, in particular pluripotency. Particular examples of reprogramming factors include OCT4, SOX2, c-MYC, KLF4, LIN28, and NANOG.

According to the invention, the term "genomic engineering proteins" relates to proteins which are able to insert, delete or replace DNA in the genome of a subject. Particular examples of genomic engineering proteins include meganucleases, zinc finger nucleases (ZFNs), transcription activator-like effector nucleases (TALENs), and clustered regularly spaced short palindromic repeat-CRISPR-associated protein 9 (CRISPR-Cas9).

According to the invention, the term "blood proteins" relates to peptides or proteins which are present in the blood plasma of a subject, in the particular blood plasma of a healthy subject. Blood proteins have diverse functions such as transport (e.g., albumin, transferrin), enzymatic activity (e.g., thrombin or ceruloplasmin), blood clotting (e.g., fibrinogen), defense against pathogens (e.g., complement components and immunoglobulins), protease inhibitors (e.g., alpha 1-antitrypsin), etc. Particular examples of blood proteins include thrombin, serum albumin, Factor VII, Factor VIII, insulin, Factor IX, Factor X, Factor XII, tissue plasminogen activator, protein C, von Willebrand factor, antithrombin III, glucocerebrosidase, erythropoietin, granulocyte colony stimulating factor (G-CSF), modified Factor VIII, and anticoagulants.

According to the invention, the term "protein replacement therapy" relates to a medical treatment which supplements or replaces a peptide or protein which has a decreased activity in a patient compared to a healthy subject. The decreased activity (including zero activity which may be the case when the peptide or protein is wholly absent in the patient) may be the result of (i) a decreased expression of the peptide or protein (i.e., the peptide or protein is fully functional but the amount thereof is decreased) or (ii) the presence of one or more mutations in the amino acid sequence of the expressed peptide or protein (i.e., the peptide or protein is not fully functional). For example, this decreased activity of the peptide or protein may be the result of a gene encoding the peptide or protein but containing one or more mutations in such a manner that (i) the expression of said gene is decreased or silenced thereby resulting in a decreased amount of the peptide or protein (which may still be fully functional) and/or (ii) the amino acid sequence of the peptide or protein encoded by said gene contains one or more mutations thereby resulting in a non-fully functional (or non-functional) peptide or protein. Diseases or disorders caused by a decreased activity of a peptide or protein in a patient may be treated by replacing or supplementing the peptide or protein (protein replacement therapy), e.g., by administering to a patient having such a disease or disorder an RNA (in particular an RNA of the present invention) comprising a nucleotide sequence encoding the peptide or protein. The nucleotide sequence encoding the peptide or protein may be autologous or heterologous to the patient. However, if the decreased activity of the peptide or protein in a patient is due to one or more mutations (i.e., resulting in a non-fully functional (or non-functional) peptide or protein), it is preferred that the nucleotide sequence encoding the peptide or protein is heterologous to the patient, in particular is obtained from a healthy subject (of the same species) expressing the peptide or protein in its native (i.e., unmutated) form. For example, such protein replacement therapy may comprise the step of administering to a patient (i) an RNA (in particular an RNA of the present invention) comprising a nucleotide sequence encoding said peptide or protein (wherein said nucleotide sequence preferably is heterologous and may be obtained from a healthy subject) or (ii) a composition, e.g., a pharmaceutical composition, comprising such RNA, or alternatively, the steps of (a) transferring an RNA (in particular an RNA of the present invention) comprising a nucleotide sequence encoding said peptide or protein (wherein said nucleotide sequence preferably is heterologous and may be obtained from a healthy subject) into a cell (wherein said cell may be autologous to the patient) and (b) administering said transfected cell to the patient. In alternative (i), the RNA is preferably taken up into cells (e.g., antigen-presenting cells, such as monocytes, macrophages, or dendritic cells, or other cells), and a translation product of the nucleotide sequence encoding a peptide or protein is formed (and optionally post-translationally modified) to yield the peptide or protein. In alternative (ii), after administration of the transfected cells to the patient, the transfected cells preferably express the peptide or protein.

The term "genome engineering" relates to the process in which DNA is inserted, deleted or replaced in the genome of a subject, preferably by using genomic engineering proteins. Particular examples of genomic engineering proteins include meganucleases, zinc finger nucleases (ZFNs), transcription activator-like effector nucleases (TALENs), and clustered regularly spaced short palindromic repeat-CRISPR-associated protein 9 (CRISPR-Cas9).

In one aspect, the present invention discloses an mRNA comprising, in the 5' to 3' direction:
  a) at least one 5'UTR element, said 5'UTR element comprising polynucleotides comprising any one of SEQ ID NOs. 1-63, 72-84; and
  b) at least one open reading frame (ORF) encoding a peptide or protein of interest.

Preferably, the isolated nucleic acid of the present invention further comprises a 3'UTR element (such as a sequence comprising SEQ ID NO:87) and a polyA sequence.

In another aspect, said 5'UTR element comprises polynucleotides comprising any one of SEQ ID Nos. 38, 43, 46, 61 or 72.

Preferably, the cytokine is an interleukin, more preferably, said interleukin is IL-12, more preferably, said IL-12 is hIL-12, and most preferably, said hIL-12 coding sequence comprises SEQ ID NO:69 or SEQ ID NO:65.

Preferably, the HPV coding sequence comprises SEQ ID NO: 85.

In another aspect, the mRNA comprises SEQ ID NO:68 or SEQ ID NO:86.

In one aspect, the mRNA comprises at least one modified or non-naturally occurring nucleotide.

In another aspect, the at least one modified or non-naturally occurring nucleotide comprises at least one backbone modification, sugar modification or base modification.

In another aspect, the at least one modified or non-naturally occurring nucleotide comprises at least one base modification.

In another aspect, at least one base modification is selected from the group consisting of: 2-amino-6-chloropurine riboside 5' triphosphate, 2-aminoadenosine 5' triphosphate, 2-thiocytidine 5' triphosphate, 2-thiouridine 5' triphosphate, 4-thiouridine 5' triphosphate, 5-aminoallylcytidine 5' triphosphate, 5-aminoallyluridine 5' triphosphate, 5-bromocytidine 5' triphosphate, 5-bromouridine 5' triphosphate, 5-iodocytidine 5' triphosphate, 5-iodouridine 5' triphosphate, 5-methylcytidine 5' triphosphate, 5-methyluridine 5' triphosphate, 6-azacytidine 5' triphosphate, 6-azauridine 5' triphosphate, 6-chloropurine riboside 5'-triphosphate, 7-deazaadenosine 5' triphosphate, 7-deazaguanosine 5' triphosphate, 8-azaadenosine 5' triphosphate, 8-azidoadenosine 5' triphosphate, benzimidazole riboside 5' triphosphate, $N^1$-methyladenosine 5' triphosphate, $N^1$-methylguanosine 5' triphosphate, $N^6$-methyladenosine 5' triphosphate, $O^6$-methylguanosine 5' triphosphate, $N^1$-methylpseudouridine 5' triphosphate, puromycin xanthosine 5' triphosphate, and pseudouridine 5'triphosphate.

In another aspect, at least one modified or non-naturally occurring nucleotide is $N^1$-methyl-pseudouridine 5' triphosphate.

In one aspect, the present invention discloses a vector comprising, in the 5' to 3' direction:
  a) at least one 5'UTR element, said 5'UTR element comprising polynucleotides comprising any one of SEQ ID NOs. 1-63, 72-84; and
  b) at least one open reading frame (ORF) encoding a peptide or protein of interest.

Preferably, the isolated nucleic acid of the present invention further comprises a 3'UTR element (such as a sequence comprising SEQ ID NO:87) and a polyA sequence.

In another aspect, said 5'UTR element comprises polynucleotides comprising any one of SEQ ID NOs. 38, 43, 46, 61 or 72.

Preferably, the cytokine is an interleukin, more preferably, said interleukin is IL-12, more preferably, said IL-12 is hIL-12, and most preferably, said hIL-12 coding sequence comprises SEQ ID NO:69 or SEQ ID NO:65.

Preferably, the HPV coding sequence comprises SEQ ID NO:85.

In another aspect, the vector comprises SEQ ID NO:68 or SEQ ID NO:86.

In one aspect, the present invention discloses a cell comprising the isolated nucleic acid sequence, the mRNA, or the vector of the present invention.

In one aspect, the present invention discloses a pharmaceutical composition comprising the isolated nucleic acid sequence, the mRNA, the vector, or the cell of the present invention. In another aspect, the pharmaceutical composition of the present invention further comprises one or more pharmaceutically acceptable excipients, and more preferably further comprises one or more additional/supplementary active compounds.

In one aspect, the present invention discloses a pharmaceutical composition as specified herein for use in therapy. For example, the pharmaceutical compositions of the present invention may be used in protein replacement therapy, genome engineering therapy, genomic reprogramming therapy, or immunotherapy.

The pharmaceutical compositions of the invention may be administered to an individual by any route, preferably parenterally. The expressions "parenteral administration" and "administered parenterally" as used herein mean modes of administration other than enteral administration ("enteral administration" and "administered enterally" as used herein mean that the drug administered is taken up by the stomach and/or the intestine). Parenteral administration is usually by injection and/or infusion and includes, without limitation, intravenous, intramuscular, intraarterial, intrathecal, intracapsular, intraosseous, intraorbital, intracardiac, intranodal, intradermal, intraperitoneal, transtracheal, subcutaneous, subcuticular, intraarticular, subcapsular, intracerebral, intracerebroventricular, subarachnoid, intraspinal, epidural intrasternal, and topical administration. For applications other than immunotherapy (e.g., for protein replacement therapy, genome engineering therapy, or genetic reprogramming therapy), it is preferred that the pharmaceutical composition of the invention is administered intraperitoneally, intramuscularly, or intradermally. For immunotherapeutic applications, it is preferred that the pharmaceutical composition of the invention is administered intravenously, intraperitoneally, intramuscularly, subcutaneously, intralymphatically, intradermally or intranodally, more preferably intradermally or intranodally, e.g., by intranodal injection.

In one aspect, the present invention discloses a method for treating or preventing a disorder comprising administering the isolated nucleic acid molecule, the mRNA, the vector, the cell or the pharmaceutical composition of the present invention to a subject in need thereof, preferably to a human patient.

Illustrative applications of protein replacement therapy for the isolated nucleic acids, mRNA, vectors, cells, and pharmaceutical compositions of the present invention include the treatment (including prophylactic treatment) of a condition, disorder or disease caused by a decreased activity of a peptide or protein, e.g., anemia (replacement protein: e.g., erythropoietin), diabetes (replacement protein: e.g., vasopressin), congenital lung disease (replacement protein: e.g., surfactant protein B), asthma (replacement protein: e.g., FOXP3), myocardial infarction (replacement protein: e.g., VEGFA), melanoma (replacement protein: e.g., BAX), autoimmune diabetes (replacement protein: e.g., IL-4), autoimmune myocarditis (replacement protein: e.g., IL-10), inflammation (replacement proteins: e.g., P-selectin glycoprotein ligand-1 (PSGL-1), Sialyl-Lewisx (SLeX), and IL-10), factor VII deficiency (replacement protein: e.g., factor VIIa), hemophilia A (replacement protein: e.g., factor VIII), hemophilia B (replacement protein: e.g., factor IX), factor X deficiency (replacement protein: e.g., factor X), factor XI deficiency (replacement protein: e.g., factor XI), factor XIII deficiency (replacement protein: e.g., factor XIII), von Willebrand disease (replacement protein: e.g., von Willebrand factor), protein C deficiency (replacement protein: e.g., protein C), antithrombin deficiency (replacement protein: e.g., antithrombin III), fibrinogen deficiency (replacement protein: e.g., fibrinogen), hereditary angioedema (replacement protein: e.g., C1-esterase inhibitor), a1-PI deficiency (replacement protein: e.g., alpha-1 proteinase inhibitor), Gaucher disease (replacement protein: e.g., glucocerebrosidase), mucopolysaccharidosis I (replacement protein: e.g., alpha-L-iduronidase), mucopolysaccharidosis II (replacement protein: e.g., iduronate sulfatase), mucopolysaccharidosis VI (replacement protein: e.g., N-acetylgalactosamine-4-sulfatase), mucopolysaccharidosis IVA (replacement protein: e.g., N-acetylgalactosamine-6-sulfatase), mucopolysaccharidosis IIIA (replacement protein: e.g., heparan sulfate sulfatase), Fabry disease (replacement protein: e.g., alpha-galactosidase A), Pompe disease (replacement protein: e.g., alpha-glucosidase), Niemann-Pick type B disease (replacement protein: e.g., acid sphingomyelinase), alpha-mannosidosis (replacement protein: e.g., alpha-mannosidase), metachromatic leukodystrophy (replacement protein: e.g., arylsulphatase A), LAL deficiency (replacement protein: e.g., lysosomal acid lipase (LAL)), sucraseisomaltase deficiency (replacement protein: e.g., sucrose-isomaltase), ADA deficiency (replacement protein: e.g., adenosine deaminase (ADA)), primary IGF-1 deficiency (replacement protein: e.g., insulin-like growth factor 1 (IGF-1)), hypophosphatasia (replacement protein: e.g., alkaline phosphatase), and acute intermittent *porphyria* (replacement protein: e.g., porphobilinogen deaminase).

Illustrative applications of genome engineering therapy for the isolated nucleic acids, mRNA, vectors, cells, and pharmaceutical compositions of the present invention include the treatment (including prophylactic treatment) of a condition, disorder or disease selected from the group consisting of X-linked severe combined immunodeficiency (X-SCID) (correction with DNA encoding the interleukin-2 receptor common gamma chain (IL-2Ry)), Xeroderma pigmentosum (correction with native, i.e., unmutated DNA), and the conditions, disorders and diseases specified above with respect to illustrative applications of protein replacement therapy. A further genome engineering therapy for the RNA or pharmaceutical compositions of the present invention includes genome editing making use of, e.g., CRISPR/CAS.

Illustrative immunotherapeutic applications for the pharmaceutical compositions of the present invention include the treatment (including prophylactic treatment) of a condition, disorder or disease selected from the group consisting of infectious diseases (e.g., those caused by a pathogen such as viruses (such as human papillomavirus (HPV), Monkeypox virus, influenza virus (A, B, or C), CMV, RSV, SARS-CoV-1, SARS-CoV-2 or MERS-CoV), bacteria, fungi or other microorganisms); an undesirable inflammation (such as an immune disorder); and cancer (such as triple negative breast cancer).

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e., a swelling or lesion formed by an abnormal growth of cells (called neoplastic cells or tumor cells), but some, like leukemia, do not. The term "cancer" according to the invention comprises triple negative breast cancer, leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are triple negative breast cancer, lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

Examples of cancers treatable with the isolated nucleic acids, mRNA, vectors, cells, and pharmaceutical compositions of the present invention include malignant melanoma, all types of carcinoma (triple negative breast cancer, colon, renal cell, bladder, prostate, non-small cell and small cell lung carcinoma, etc.), lymphomas, sarcomas, blastomas, gliomas, etc.

Exemplary immune disorders include, but are not limited to, autoimmune diseases (for example, diabetes mellitus, arthritis (including rheumatoid arthritis, juvenile rheumatoid arthritis, osteoarthritis and psoriatic arthritis), multiple sclerosis, encephalomyelitis, myasthenia gravis, systemic lupus erythematosus, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, sepsis and septic shock, inflammatory bowel disorder, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, glomerulonephritis, idiopathic sprue, lichen planus, Graves' disease, sarcoidosis, primary biliary cirrhosis, uveitis posterior, and interstitial lung fibrosis), graft-versus-host disease, cases of transplantation, and allergy such as atopic allergy.

Exemplary viruses include, but are not limited to, human papillomavirus (HPV), Monkeypox virus, human immunodeficiency virus (HW), Epstein-Barr virus (EBV), cytomegalovirus (CMV) (e.g., CMV5), human herpesviruses (HHV) (e.g., HHV6, 7 or 8), herpes simplex viruses (HSV), bovine herpes virus (BHV) (e.g., BHV4), equine herpes virus (EHV) (e.g., EHV2), human T-Cell leukemia viruses (HTLV)5, Varicella-Zoster virus (VZV), measles virus, papovaviruses (JC and BK), hepatitis viruses (e.g., HBV or HCV), myxoma virus, adenovirus, parvoviruses, polyoma virus, influenza viruses (e.g., influenza virus A, influenza virus B, or influenza virus C), respiratory syncytial virus (RSV), papillomaviruses and poxviruses such as vaccinia virus, molluscum contagiosum virus (MCV), and lyssaviruses. Such viruses may or may not express an apoptosis inhibitor. Exemplary diseases caused by viral infection include, but are not limited to, chicken pox, Cytomegalovirus infections, genital herpes, Hepatitis B and C, influenza, shingles, and rabies.

Exemplary bacteria include, but are not limited to, *Campylobacter jejuni, Enterobacter species, Enterococcus faecium, Enterococcus faecalis, Escherichia coli* (e.g., *E. coli* O157:H7), Group A streptococci, *Haemophilus influenzae, Helicobacter pylori, listeria, Mycobacterium tuberculosis, Pseudomonas aeruginosa, S. pneumoniae, Salmonella, Shigella, Staphylococcus aureus, Staphylococcus epidermidis, Borrelia*, and *Rickettsia*. Exemplary diseases caused by bacterial infection include, but are not limited to, anthrax, cholera, diphtheria, foodborne illnesses, leprosy, meningitis, peptic ulcer disease, pneumonia, sepsis, septic shock, syphilis, tetanus, tuberculosis, typhoid fever, urinary tract infection, Lyme disease, and Rocky Mountain spotted fever.

Particular examples of infectious diseases treatable with the isolated nucleic acid, RNA or pharmaceutical compositions of the present invention include viral infectious diseases, such as human papillomavirus (HPV) infection or related diseases, Monkeypox, AIDS (HW), hepatitis A, B or C, herpes, herpes zoster (chicken-pox), German measles (rubella virus), yellow fever, dengue fever; infectious diseases caused by flaviviruses; influenza; infectious diseases caused by RSV; infectious diseases caused by CMV; hemorrhagic infectious diseases (Marburg or Ebola viruses); bacterial infectious diseases (such as Legionnaire's disease (*Legionella*), gastric ulcer (*Helicobacter*), cholera (*Vibrio*), infections by *E. coli*, Staphylococci, *Salmonella* or Streptococci (tetanus); infections by protozoan pathogens such as malaria, sleeping sickness, leishmaniasis, toxoplasmosis, i.e. infections by *Plasmodium, Trypanosoma, Leishmania* and *Toxoplasma*; or fungal infections, which are caused, e.g., by *Cryptococcus neoformans, Histoplasma capsulatum, Coccidioides immitis, Blastomyces dermatitidis* or *Candida albicans*.

Particular examples of diseases treatable with the isolated nucleic acid, RNA or pharmaceutical compositions of the present invention include precancerous lesions (such as cervical precancerous lesions), cancer (such as triple negative breast cancer), condylomata acuminate, or other HPV infection or HPV infection-related diseases or conditions (such as HPV-associated cervical cancer).

EXAMPLES

Example 1 Characterization of 5'UTR Sequences

Novel 5'UTR sequences generated and tested in this study are listed (Table 1). All of these sequences were designed manually to achieve high MRL scores as predicted using the Optimus 5-Prime program.

TABLE 1

Novel 5'UTR sequences

| SEQ ID | Name of 5' UTR Sequence | Sequence (5'→3') | Length | MRL score |
|---|---|---|---|---|
| 1 | 1 | AGGGAAATAAGAAGAGTAAGAAGAAATATAAGAGCCACC | 39 | 6.015 |
| 2 | 2 | AGGGCAGCCACTTTGCACTGGAACTTACAACACCCGAGCAAGGACGCGACTCTGAAGAAATATAAGAGCCACC | 73 | 6.325 |
| 3 | 3 | AGGGAAAATATAAACATAAACATAAACGAGATATCACGGCCGTGGTGGACGGATAATAGCCACC | 64 | 6.279 |

TABLE 1-continued

Novel 5'UTR sequences

| SEQ ID | Name of 5' UTR Sequence | Sequence (5'→3') | Length | MRL score |
|---|---|---|---|---|
| 4 | 4 | AGGGAAAATATAAACATAAACATAAACGACAAGAAACACATACAAAAGAAAC AGGACAGAAAACAGCCACC | 71 | 6.512 |
| 5 | 5 | AGGGAAAATATAAACATAAACATAAACGACAAGAAACACATACAAAAGAAAC AGGACAGAAAATAGCCACC | 71 | 6.528 |
| 6 | 6 | AGGAAAAATACACACACACACACACACACACACAAACACACACACACACA CACAAACACAAGAGCCACC | 71 | 6.413 |
| 7 | 7 | AGGAAATATAGAAAGAGAGAAAGAAAGAAAGAGAGAGAGAAAGAGAGAAAGA AAGAAAGAGCAGCGCCACC | 71 | 6.34 |
| 8 | 8 | AGGAATAATAGAGAGAGAAAGAGAGAGAGAGAAAGAGAGAGAGAGA GAGAGAGCTACGCCACC | 71 | 6.615 |
| 9 | 9 | AGGAAATACATAAACATAGAAAGAGAAAACATAACACACAACAAACACATAC AACACAAACACAACACAAACTCGCCACC | 80 | 6.16 |
| 10 | 10 | AGGAAAAATAATAACATAATCATACTACACAACTAACACATACATCACATAC ACATCACATAAATGCCACC | 71 | 5.443 |
| 11 | 11 | AGGCAATACTCAAAATCAATCATCATCACAACATCAACAATCAATCATCAAC ACATCATCAGAGAGAGAAGACACCACC | 79 | 6.519 |
| 12 | 12 | AGGGATAATACTATAACTCTCATCTCAACACTCCTCCTCATTCCAATCTCTC ACACATAATAGCCACC | 68 | 6.653 |
| 13 | 13 | AGGGAAAATATAAACATAAACATAATAAAACGACAAGAAACACATACAAAAG AAAACAGAAAACAGCCACC | 71 | 6.494 |
| 14 | 14 | AGGGCAGCCACTAATAACAAAAATAACCAACATTTAATAAAGGACGCGAAAT AGAAGAAATATAAGAGCCACC | 73 | 6.407 |
| 15 | 15 | AGGGAAAATACTAATAACAAAAATAACCAACATTTAATAAATTACATGAAAT AGAAGAAATATAAGAGCCACC | 73 | 6.099 |
| 16 | 16 | AGGGAATACACTAATAACAAAAATAACCAACATTTAATAAAAAACGTGAAAT AGAAGAAATATAAGAGCCACC | 73 | 6.425 |
| 17 | 17 | AGGGAAAATATAAACATAATGTAAAGATAGAAAAAAATTGAGAAGTTAACCG AAAAATAGATAATAGCCACC | 72 | 4.112 |
| 18 | 18 | AGGGAAAATATAAACACACACACACACATAATGTAAAGATAGAAAAAAATTGAG AAGCCGGAAGATAATAGCCACC | 74 | 4.538 |
| 19 | 19 | AGGAAAAATACACACACACAGAGAGAAAGAGAGAAACACACAAAGAGAGACA CACACACACAAACACAAGAGCCACC | 77 | 6.503 |
| 20 | 20 | AGGGAAAATATAAACACACAACATAAACATAAAAGAAACACATACAAAAGAA AGAGAGAACAGAAAATAGCCACC | 75 | 6.523 |
| 21 | 21 | AGGAAATATAGCACACAAAAAGAGAGAAAGAAAGAAACACACAGAGAAAGC ACAAAAGAAAGAAAGAGCAGCGCCACC | 79 | 6.378 |
| 22 | 22 | AGGAATAATACACACAGAGAGAAAAGTAAGAAGAGAAAGAGAGAGAAGTAAG AAATAAACGCCACC | 66 | 6.317 |
| 23 | 23 | AGGAAATACATACACACAATTAAATTCTGAATTCAATAACAAACACATATCA TTAAGACAAAAGTTAACTCGCCACC | 77 | 6.464 |
| 24 | 24 | AGGAAAAATAATAACATAATCAGAGAGAGAGAGAGAGAGAAATAAGAGATAC ATCGAGAAAACATAAATGCCACC | 75 | 5.334 |
| 25 | 25 | AGGCAATACTCAAAATCATAAACATAAACGACAACAACAATCAATCATAATA AATAAATAGAGAGAGAAGACACCACC | 78 | 6.533 |
| 26 | 26 | AGGGATAATACTATAACGAGACACACAAACAACAAAAAAAGCGCGCCACACA TAATAGCCACC | 63 | 6.41 |
| 27 | 001+ | AGGGAAATAAGAGAGAAAAGAAGAGTAAGAAGAAATATAAGAGCCACCATGG CCACCATGGCCACC | 66 | 6.497 |
| 78 | HBB | AGGGACATTTGCTTCTGACACAACTGTGTTCACTAGCAACCTCAAACAG ACACC | 54 | |

TABLE 1-continued

Novel 5'UTR sequences

| SEQ ID | Name of 5' UTR Sequence | Sequence (5'→3') | Length | MRL score |
|---|---|---|---|---|
| 28 | HBB long | AGGGCAGAGCCATCTATTGCTTACATTTGCTTCTGACACAACTGTGTTCACTAGCAACCTCAAACAGACACC | 72 | 6.679 |
| 29 | HBB short | AGACATTTGCTTCTGACACAACTGTGTTCACTAGCAACCTCAAACAGACACC | 52 | 6.555 |
| 30 | 001-30 + HBB | AGGGAAATAAGAGAGAAAAGAAGAGTAAGAACAGGGCAGAGCCATCTATTGCTTACATTTGCTTCTGACACAACTGTGTTCACTAGCAACCTCAAACAGACACC | 104 | 6.763 |
| 72 | hHBB 5UTR-kozak | AGGGAAATAAGAGAGAAAAGAAGAGTAAGAACAGGGCAGAGCCATCTATTGCTTACATTTGCTTCTGACACAACTGTGTTCACTAGCAACCTCAAACAGCCACC | 104 | 6.721 |
| 31 | miniUTR3 | AGGGAGACTGCCACC | 15 | N/A |
| 32 | miniUTR3+ | AGGGAGACTGCCACCATGGCCACCATGGCCACC | 33 | 6.063 |
| 33 | miniUTR7 | AGGGAGACTGCCAAG | 15 | N/A |
| 34 | miniUTR7+ | AGGGAGACTGCCAAGATGGCCAAGATGGCCAAG | 33 | 6.128 |
| 35 | RPL32 | AGGGCCCAAGCTGGCTAGCGGGGCGCTGCCTACGGAGGTGGCAGCCATCTCCTTCTCGGCATC | 63 | 5.581 |
| 36 | RPL32-Kozak | AGGGCCCAAGCTGGCTAGCGGGGCGCTGCCTACGGAGGTGGCAGCCATCTCCTTCTCGGCACC | 63 | 5.533 |
| 37 | RPL32-Kozak+ | AGGGCCCAAGCTGGCTAGCGGGGCGCTGCCTACGGAGGTGGCAGCCATCTCCTTCTCGGCATCGGCACC | 69 | 5.718 |
| 38 | HBB-opt | AGGTGTATTTACTAGTAACGTAACAGTGTTACGTAGTGACGTTTAACTGAGACT | 54 | 7.391 |
| 79 | HBB-opt2 | AGGTGTATTTACTAGTAACGTAACAGTGTTACGTAGTGACGTTTAACTGCCACC | 54 | 6.958 |
| 39 | HBB-opt-Kozak | AGGTGTATTTACTAGTAACGTAACAGTGTTACGTAGTGACGTTTAACTGACACC | 54 | 7.142 |
| 40 | 001-opt | AGAGTAGTAACAGTGTATCGAATCGCAATGAATCATATGAGTGACGAA | 48 | 7.649 |
| 41 | 001-opt-Kozak | AGGAGTAGTAACAGTGTATCGAATCGCAATGAATCATATGAGTGACACC | 49 | 7.464 |
| 42 | 001-opt-Kozak+ | AGGAGTAGTAACAGTGTATCGAATCGCAATGAATCATATGAGTGACGAAGCCACC | 55 | 7.335 |
| 43 | 17-opt | AGGTAACGTAATTGCATACCGTGAATATCGTAGTGAACTGAGTAGTAAACCGTTTGTTAATTAATGAGCAGT | 72 | 7.872 |
| 44 | 17-opt-Kozak | AGGTAACGTAATTGCATACCGTGAATATCGTAGTGAACTGAGTAGTAAACCGTTTGTTAATTAATAGACACC | 72 | 7.542 |
| 45 | 17-opt-Kozak+ | AGGTAACGTAATTGCATACCGTGAATATCGTAGTGAACTGAGTAGTAAACCGTTTGTTAATTAATGAGCAGTGACACC | 78 | 7.257 |
| 83 | 17-opt2 | AGGTAACGTAATTGCATACCGTGAATATCGTAGTGAACTGAGTAGTAAACCGTTTGTTAATTAATAGCCACC | 72 | 7.444 |
| 46 | 18-opt | AGGTATTACGTAACCTGTTGAATTCGTACTTGATAGCTAATCTAAAAATGAACAGTCTGAATATGATCGGAAAC | 74 | 8.495 |
| 47 | 18-opt-Kozak | AGGTATTACGTAACCTGTTGAATTCGTACTTGATAGCTAATCTAAAAGTGAACAGTCTGAATATAATCGACACC | 74 | 7.412 |
| 48 | 18-opt-Kozak+ | AGGTATTACGTAACCTGTTGAATTCGTACTTGATAGCTAATCTAAAAATGAACAGTCTGAATATGATCGGAAACGGCACC | 80 | 7.936 |
| 84 | 18-opt-nKozak | AGGTATTACGTAACCTGTTGAATTCGTACTTGATAGCTAATCTAAAAGTGAACAGTCTGAATATAATCGCCACC | 74 | 7.412 |
| 49 | hAg-kozak | ATTCTTCTGGTCCCCACAGACTCTCAGAGAGAACCCGCCACC | 42 | 6.033 |
| 50 | 1-opt | AGCGTTATGAATCGCGTAATGGACGTTATGAGCGCAGAC | 39 | 7.659 |
| 51 | 2-opt | AGTAGAGCTAGTTAACATTGTGAATTACTTAACGTTTGCTAACATGAACATGCTAGCGAATATGAGCGTGAAG | 73 | 8.533 |

TABLE 1-continued

Novel 5'UTR sequences

| SEQ ID | Name of 5' UTR Sequence | Sequence (5'→3') | Length | MRL score |
|---|---|---|---|---|
| 52 | 11-opt | AGGCGTTATTCGTAGTTAGTGAATAGCGTATCAGTTACTGTTAATCGTTAAC AGTTTAATAGCGTTAGTGACTAGTGCA | 79 | 8.146 |
| 80 | 11-opt2 | AGGGTTATTCGTAGTTAGTGAATAGCGTATCAGTTACTGTTAATCGTTA ACAGTTTAATAGCGTTAGTGACTAGTGCA | 78 | 8.127 |
| 81 | 11-opt3 | AGGAGTTATTCGTAGTTAGTGAATAGCGTATCAGTTACTGTTAATCGTT AACAGTTTAATAGCGTTAGTGACTGCCACC | 79 | 7.682 |
| 82 | 11-opt4 | AGGGTTATTCGTAGTTAGTGAATAGCGTATCAGTTACTGTTAATCGTTA ACAGTTTAATAGCGTTAGTGACTGCCACC | 78 | 7.697 |
| 53 | 12-opt | AGCGTGAACTGTTAAACCGTTATTTGAATCGCGTTATGCATTCCAATATGAA TCGCGTAATGTCTACT | 68 | 8.599 |
| 54 | 23-opt | AGCGCAGTCGTATACGCGTTAACGTAGTGTATTTAGTGACTAACGCATTTCG TTAATAGTAACGTTAACTAGTGAAG | 77 | 7.694 |
| 55 | 25-opt | AGGCGTTATTTAACGTAGTGAGCGTTAACGTTAACAGTGAACAGTCTGATTT CCGTAATGGATCGCGTAGTTAGCATG | 78 | 9.023 |
| 56 | 26-opt | AGGGATCACAGCGTAACGTTCGTGACGAATTTCGTAACCGACATGCATCGTT TAATGGATACT | 63 | 8.178 |
| 57 | HBB long-opt | AGCGTATATCCGTTTATAGCGTACTTGATCGTTTTAATGACGTTCGCAAACA TGAATCGCGTAATTAAAATG | 72 | 8.789 |
| 58 | HBB short-opt | AGTCGTTTACTAGTAGCGTATACGTTTTAATTAGTGACGTTTAACTGAGACT | 52 | 7.341 |
| 59 | 001-30+HBB-opt | AGGGTCGTAAGCCGGTAACGTAACGTAGTGAGACGGAATAGTAACGTATTGA TTACGTTTACTAGTAGCGTATCAGTGTTAATTAGTGACGTTAACTAGACGAA | 104 | 8.403 |
| 60 | BNT162b2-opt | AGTCGTTACTAGTGAACTTCCGTTTAACCGTGAATATGAATCTGATCGGAGA C | 53 | 7.875 |
| 76 | BNT162b2-opt2 | AGGAGTTACTAGTGAACTTCCGTTTAACCGTGAATATGAATCTGATCGG AGAC | 53 | 7.804 |
| 77 | BNT162b2-opt3 | AGGAGTTACTAGTGAACTTCCGTTTAACCGTGAATAGGAATCTGATCGC CACC | 53 | 7.009 |
| 61 | mRNA1273-opt | AGGTTAATAACAGTGAATCGCAGTGTGATAAAATCGTTAGTGAATGTCCGTT AATAGA | 58 | 7.574 |
| 74 | mRNA1273-opt2 | AGGGAAATAACAGTGAATCGCAGTGTGATAAAATCGTTAGTGAATATCC GTTAATAGAGCCACC | 64 | 6.894 |
| 75 | mRNA1273-opt-nKozak | AGGTTAATAACAGTGAATCGCAGTGTGATAAAATCGTTAGTGAATATCC GTTGCCACC | 58 | 7.083 |
| 62 | hAg-kozak-opt | AGTTCGTTATGAGCGTAAACATGAATATGAACGTTATCGGAAGT | 44 | 7.731 |
| 63 | HBA1 mut | AGGGTCTTCTGGTCCCCACAGACTCAGAGAGAACCCACC | 39 | 6.075 |
| 64 | 001* | AGGGAAATAAGAGAGAAAAGAAGAGTAAGAAGAAATATAAGAGCCACC | 48 | 6.174 |
| 66 | BNT UTR | GGGCGAACTAGTATTCTTCTGGTCCCCACAGACTCAGAGAGAACCCGCC ACC | 52 | |
| 76 | BNT162b2 | AGAATAAACTAGTATTCTTCTGGTCCCCACAGACTCAGAGAGAACCCGC CACC | 53 | 6.293 |
| 67 | Moderna UTR | GGGAAATAAGAGAGAAAAGAAGAGTAAGAAGAAATATAAGAGCCACC | 47 | |
| 73 | mRNA1273 | AGGGAAATAAGAGAGAAAAGAAGAGTAAGAAGAAATATAAGACCCCGGC GCCGCCACC | 58 | |

*5'UTR 001 (SEQ ID NO. 64) is SEQ ID NO. 20 disclosed in WO2013071047A1.

The secondary structures of 5'UTR sequences tested in this study were predicted using the RNA Folding Form V2.3 program (http://www.unafold.orgimfoldiapplicationsirna-folding-form-v2.php). The predicted secondary structures of 5'UTR sequences tested in this study have the greatest negative delta G.

Example 2 Modulation of Translational Efficiency of FLuc Gene by 5'UTR Sequence Optimization Firefly luciferase gene (FLuc) is broadly used as a reporter gene to study UTR-regulated transcription and translation. FLuc gene (NCBI GeneBank: MK484107.1) with various 5'UTR sequences was cloned using a T7 expression plasmid vector in which the FLuc gene is expressed under the control of the T7 promoter. Capped FLuc mRNA was generated by in vitro transcription using the HiScribe™ T7 High Yield RNA Synthesis Kit (NEB, Ipswich, MA) and CleanCap AG (Trilink, San Diego, CA). To measure the efficiency of FLuc mRNA translation, 500 ng of FLuc mRNA was transfected in HeLa cells (ATCC, Manassas, VA) using Lipofectamine MessengerMAX (Thermo Fisher Scientific, Waltham, MA), following manufacturer's instructions. After 24-h incubation, the level of FLuc proteins was determined indirectly by measuring luciferase activity using the Bio-Lite Luciferase Assay System (Vazyme, Nanjing, China). The relative luciferase activity was normalized to that of FLuc mRNA containing the 5'UTR sequence of Moderna's COVID vaccine mRNA-1273.

As shown in FIG. 1, FLuc mRNA containing novel 5'UTR sequences 2, 001-opt, 17-opt, 18-opt, or HBB-opt produced 1.5 to 2.7-fold more FLuc proteins than FLuc mRNA containing the 5'UTR sequence of mRNA-1273, whereas FLuc mRNA containing novel 5'UTR sequences 8, 17, 18, and 24 produced 0.5 to 0.6-fold less FLuc proteins than FLuc mRNA containing the 5'UTR sequence of mRNA-1273.

Interestingly, MRL scores were not directly correlated with the efficiency of FLuc mRNA translation. Furthermore, there is no significant relationship between mRNA secondary structure and translation efficiency.

Example 3 Comparison of Transcription Efficiency of FLuc Gene Containing Various 5'UTR Sequences To determine the impact of 5'UTR sequences on the transcription efficiency of FLuc gene, 0.5 μg of expression plasmid containing FLuc gene with various 5'UTR sequences under the control of T7 promoter was transcribed in vitro using the HiScribe™ T7 High Yield RNA Synthesis Kit (NEB). After 2-h in vitro transcription reaction, plasmid templates were digested with DNase I, followed by purification of mRNA using magnetic beads (Yeasen, Shanghai, China). The quantity of mRNA was measured using a NanoDrop spectrophotometer (Thermo Fisher Scientific). The amount of FLuc mRNA transcripts was normalized to that of FLuc gene containing the 5'UTR sequence of Moderna's COVID vaccine mRNA-1273.

Figure 2:
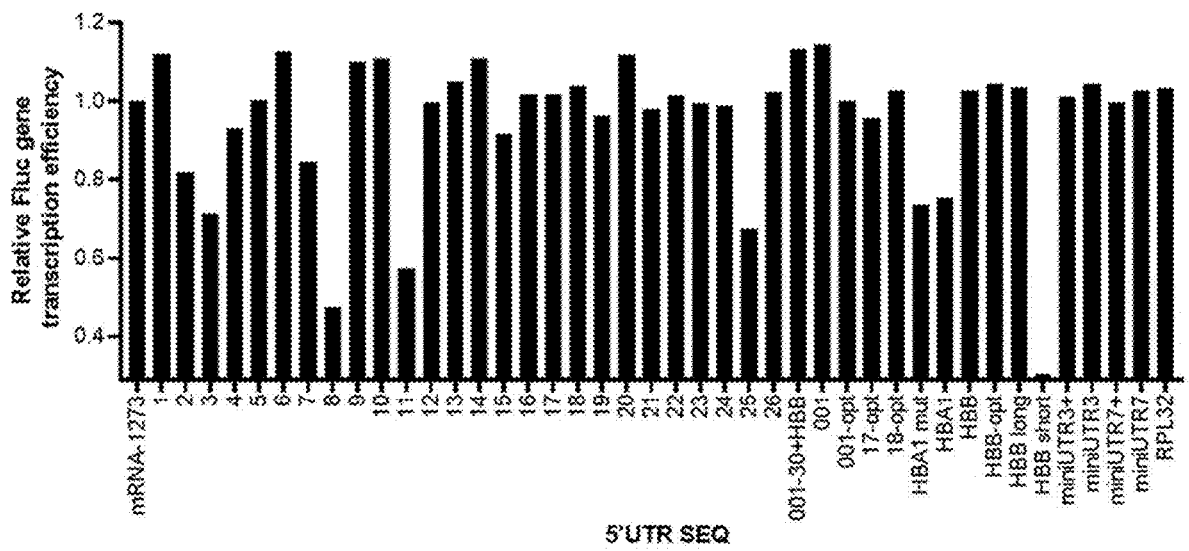
FIG. 2 Comparison of transcription efficiency of FLuc gene containing various 5'UTR sequences.

As shown in FIG. 2, FLuc genes containing new 5'UTR sequence 1, 4, 5, 6, 9, 10, 12, 13, 14, 15, 16, 17, 18, 19, 20, 21, 22, 23, 24, 26, 001-30+HBB, 001, 001-opt, 17-opt, 18-opt, HBB-opt, HBB long, miniUTR3+, miniUTR3, min-iUTR7+, miniUTR7, or RPL32 produced FLuc mRNA transcripts comparable to FLuc gene containing the 5'UTR sequence of mRNA-1273.

Interestingly, FLuc genes containing new 5'UTR sequences 2, 3, 7, 8, 11, 25, HBA1 mut, and HBB short produced 0.2 to 0.7-fold less FLuc mRNA transcripts than FLuc gene containing the 5'UTR sequence of mRNA-1273.

Example 4 Comparison of Translation Efficiency of Human scIL-12 mRNA Containing Various Sequences Single chain interleukin 12 (scIL-12) mRNA has been previously developed as an anti-tumor cytokine mRNA therapy for solid cancers (Etxeberria I et al. Cancer Cell. 2019. 36:613; Lieschke G J et al. Nat Biotech. 1997. 15:35). Human scIL-12 gene (SEQ ID NO.65) with various 5'UTR sequences was cloned using a T7 expression plasmid vector. Capped scIL-12 mRNA was generated by in vitro transcription using the HiScribe™ T7 High Yield RNA Synthesis Kit and CleanCap AG.

To measure the efficiency of scIL-12 mRNA (the coding sequence of scIL-12 is SEQ ID NO.65) translation, 500 ng of scIL-12 mRNA was transfected in HeLa cells using Lipofectamine MessengerMAX, following manufacturer's instructions. After 24-h incubation, the level of scIL-12 proteins was measured using a human IL-12 ELISA kit (Bio-Techne, Minneapolis, MN). The amount of IL-12 proteins produced by HeLa cells transfected with scIL-12 mRNA containing various 5'UTR sequences was normalized to that produced by the cells transfected with scIL-12 mRNA containing the 5'UTR sequence of Biontech's COVID vaccine BNT162b2.

Figure 3:
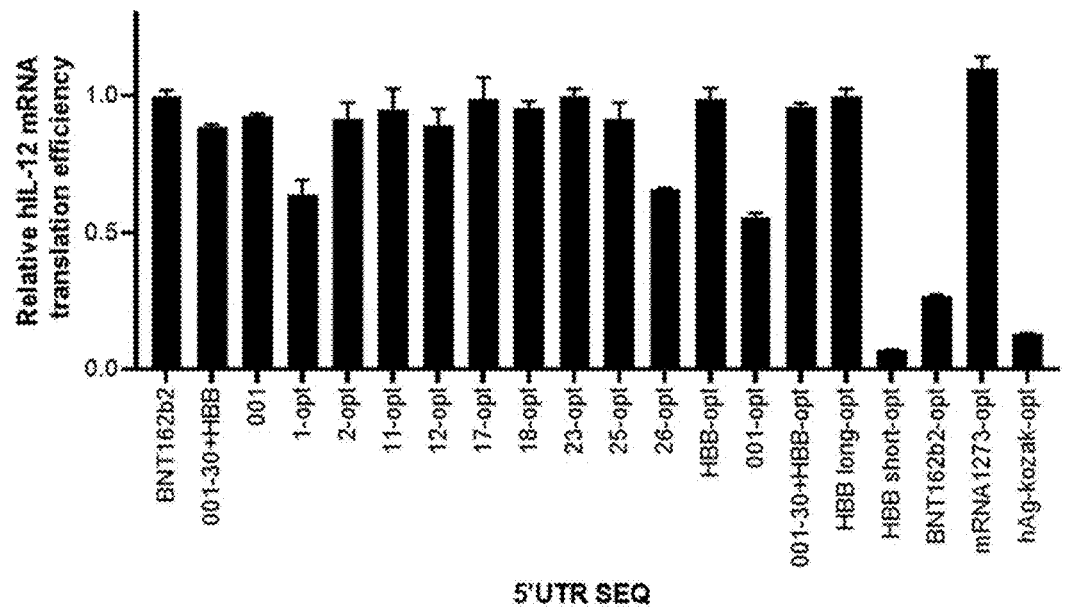
FIG. 3 Comparison of translation efficiency of human scIL-12 mRNA containing various 5'UTR sequences.

As shown in FIG. 3, all novel 5'UTR sequences except 1-opt, 26-opt, 001-opt, HBB short-opt, BNT162b2-opt, and hAg Kozak-opt show comparable or higher translation efficiency to the 5'UTR sequence of BNT162b2.

Novel 5'UTR sequences 001-opt, HBB short-opt, BNT162b2-opt, and hAg Kozak-opt significantly decrease translation efficiency of scIL-12 mRNA compared to the 5'UTR sequence of BNT162b2.

Example 5 Comparison of Translation Efficiency of Human scIL-12 mRNA Containing Various Sequences We transfected Hela cells with 0.5 μg of different human (h) IL-12 mRNA molecules with MessengerMax, including our high translation (H-T) hGL-001 sequence (the hGL-001 sequence is SEQ ID NO:68, and the hIL12 coding sequence is SEQ ID NO:69), and sequences with UTRs derived from Moderna's (hMD-001) (SEQ ID NO:71) and BioNTech's (hBT-001) (SEQ ID NO:70) COVID vaccines (Biontech Patent Application: WO2018160540A1, Moderna Patent Application: WO2017201350A1, Reference: Hewitt S L etc. Intratumoral IL12 mRNA Therapy Promotes TH1 Transformation of the Tumor Microenvironment. Clin Cancer Res. 2020 Dec. 1; 26(23):6284-6298. doi: 10.1158/1078-0432.CCR-20-0472. Epub 2020 Aug. 17. PMID: 32817076).

Figure 6:
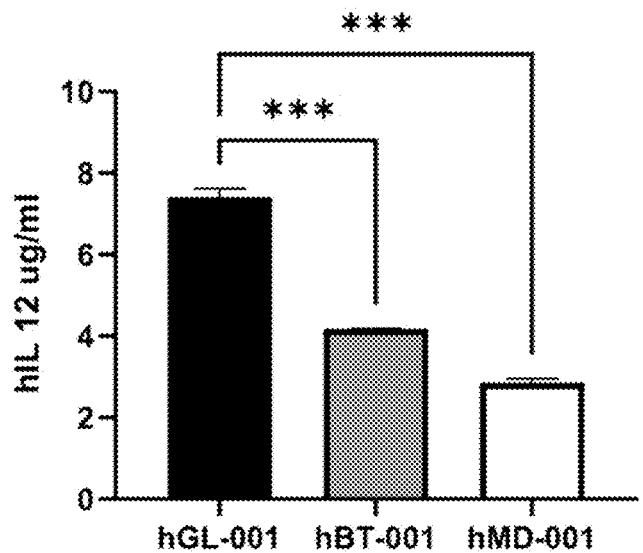
FIG. 6 Comparison of translation efficiency of human scIL-12 mRNA containing various 5'UTR sequences.

The protein expression in the cell supernatants was quantified by ELISA. As shown in FIG. 6, the hGL-001 delivered 1.8 and 2.6-fold higher expression than hBT-001 and hMD-001, respectively.

Example 6 Comparison of Transcription Efficiency of Human scIL-12 Gene Containing Various 5'UTR Sequences To determine the impact of 5'UTR sequences on transcription efficiency of human scIL-12 gene (the coding sequence of human scIL-12 is SEQ ID NO.65), 0.5 µg of the expression plasmid containing human scIL-12 gene (Etxeberria I et al. Cancer Cell. 2019. 36:613) with various 5'UTR sequences under the control of T7 promoter was transcribed in vitro using the HiScribe™ T7 High Yield RNA Synthesis Kit (NEB). After 2-h in vitro transcription reaction, mRNA was purified using magnetic beads (Yeasen) following digestion of plasmid templates with DNase I. The quantity of mRNA was measured using a NanoDrop spectrophotometer. The amount of scIL-12 mRNA transcripts expressed from scIL-12 genes containing various novel 5'UTR sequences was normalized to that expressed from scIL-12 gene containing the 5'UTR sequence of BNT162b2.

Figure 4:
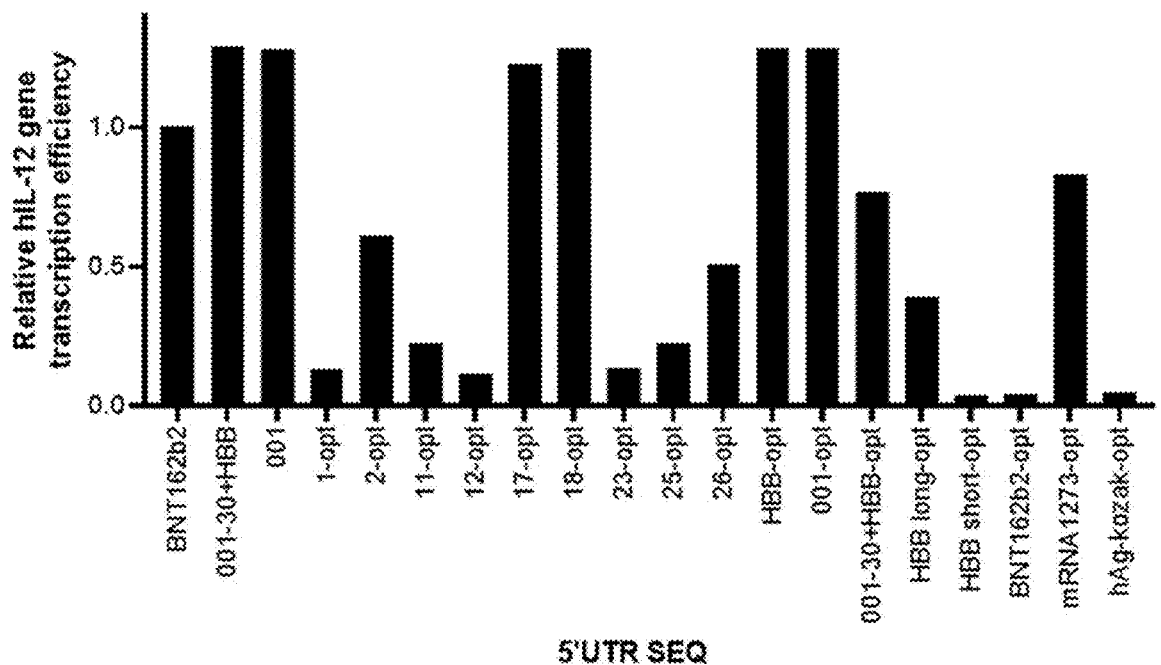
FIG. 4 Comparison of transcription efficiency of human scIL-12 gene containing various 5'UTR sequences.

As shown in FIG. 4, Human scIL-12 genes containing novel 5'UTR sequence 001-30+HBB, 001, 17-opt, 18-opt, HBB-opt, or 001-opt produced 0.2 to 0.3-fold greater scIL-12 mRNA transcripts than that containing the 5'UTR sequence of BNT162b2. 5'UTR sequences 1-opt, 2-opt, 11-opt, 12-opt, 23-opt, 25-opt, 26-opt, HBB long-opt, HBB short-opt, BNT162b2-opt, and hAg Kozak-opt have 0.4 to 0.8-fold reduced transcription efficiency of human scIL-12 gene than the 5'UTR sequence of BNT162b2, suggesting that 5'UTR sequences 1-opt, 2-opt, 11-opt, 12-opt, 23-opt, 25-opt, 26-opt, HBB long-opt, HBB short-opt, BNT162b2-opt, and hAg Kozak-opt have more potent regulatory activity over transcription of human scIL-12 gene than the 5'UTR sequence of BNT162b2.

Example 7 Comparison of Translation Efficiency of HPV mRNA Containing Various 5'UTR Sequences An HPV antigenic polypeptide coding sequence with various 5'UTR sequences, as indicated in the list, was cloned using a T7 expression plasmid vector. Capped HPV mRNA was generated by in vitro transcription using T7 polymerase (Roche) and Clean Cap AG (Trilink). The coding sequence of HPV antigenic polypeptide sequence is SEQ ID NO:85. The mRNA sequence comprising HBB-opt 5'UTR (SEQ ID NO:38) and HPV antigenic polypeptide coding sequence is SEQ ID NO:86.

To measure the efficiency of HPV mRNA translation, 500 ng of HPV mRNA was transfected in 293 Hek cells using lipofectamine MessengerMAX, following the manufacturer's instructions. After 48-h (FIG. 7) or 24-h (FIG. 8A)/48-h (FIG. 8B)/72-h (FIG. 8C) incubation, the levels of HPV proteins were measured using flow cytometry with an anti-E7-PE conjugated antibody (Santa Cruz Biotechnology). Flow cytometry analysis was performed on an Attune NxT Focusing Cytometer (ThermoFisher Scientific). Data analysis was performed using FlowJo software (BD Life Sciences). To quantify the results, the percentage of positive cells was graphed using Prism 4 (GraphPad Software, Inc.).

Figure 7:
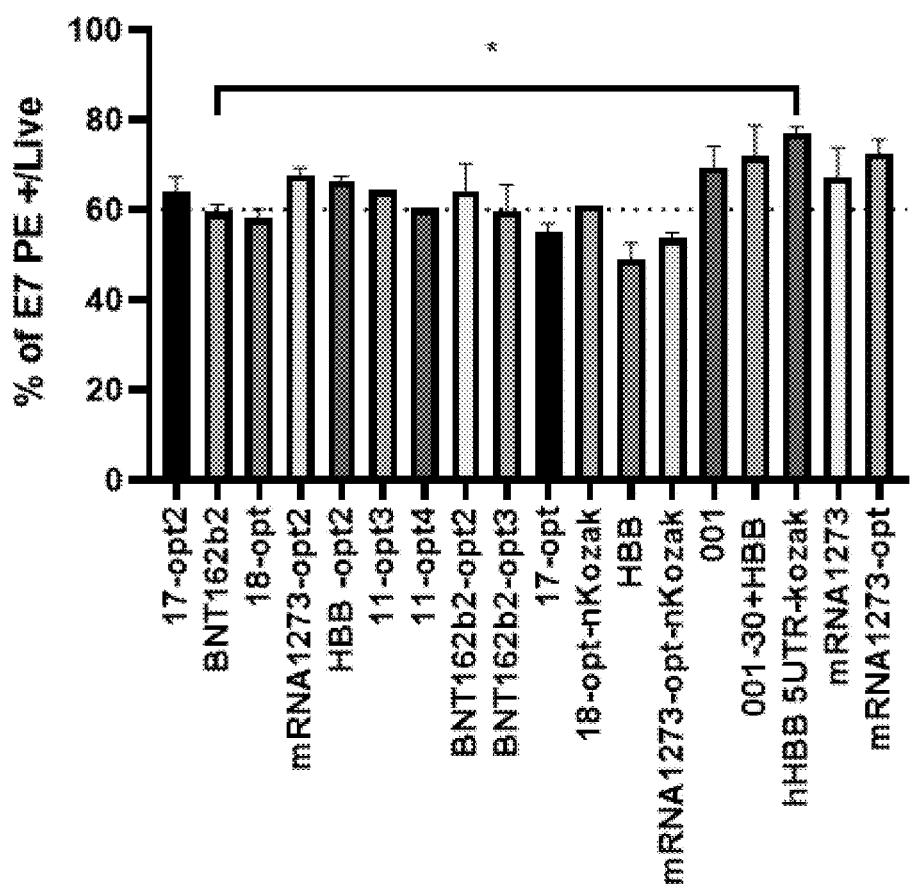
FIG. 7 Comparison of translation efficiency of HPV mRNA containing various 5'UTR sequences.
Figure 8A:
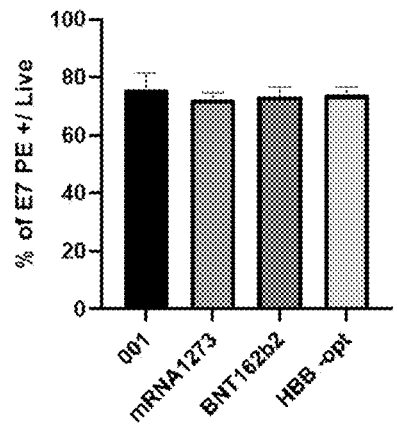
FIG. 8A, 8B, 8C Comparison of translation efficiency of HPV mRNA containing various 5'UTR sequences.
Figure 8B:
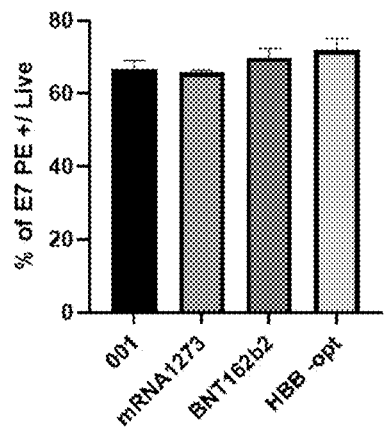
Figure 8C:
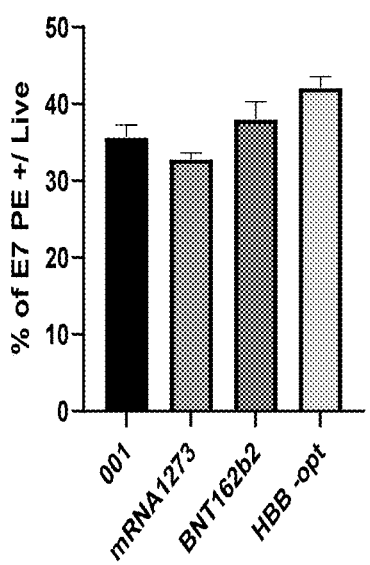

As shown in FIG. 7, BNT162b2 is BioNtech's Lead 5'UTR used in its commercialized COVID-19 vaccine. Thus, among the 5' UTRs that were screened compared to BioNtech's 5' UTR (BNT162b2), hHBB UTR-kozak (SEQ ID NO:72) significantly improved the translational efficiency of HPV antigenic polypeptide coding sequence.

As shown in FIG. 8, as expected, protein expression decreased over time in all groups. At 72 h post-transfection, Geneleap's HPV mRNA with HBB-opt 5'UTR showed increased E7 protein expression compared to benchmark 5'UTRs. No significant difference in E7 protein expression was observed at 24 h and 48 h post-translation.

Example 8 Comparison of IFN-γ Production by Human PBMCs Stimulated with Culture Supernatants of scIL-12 mRNA-Transfected HeLa Cells We determined whether scIL-12 proteins produced by HeLa cells transfected with human scIL-12 mRNA (the coding sequence of human scIL-12 is SEQ ID NO.65) containing the aforementioned 5'UTR variants have biological activity and if the level of biological activity is positively correlated with the level of translation efficiency of human scIL-12 mRNA. To this end, human PBMCs were plated in 96-well plates, followed by treatments with species-specific anti-CD3c antibody (1 µg/ml, Biolegend, San Diego, CA) in the presence or absence of 50 µl of culture supernatants of HeLa cells transfected with scIL-12 mRNA for 3 days. To determine the correlation between the biological activity of scIL-12 proteins expressed from scIL-12 mRNA and the translation efficiency of scIL-12 mRNA, the culture supernatants of HeLa cells transfected with scIL-12 mRNA were diluted with various dilution factors with PBS. After 3-day incubation, culture supernatants of PBMCs were collected for human IFN-γ measurement by ELISA (Biotechne) according to the manufacturer's instructions.

Figure 5:
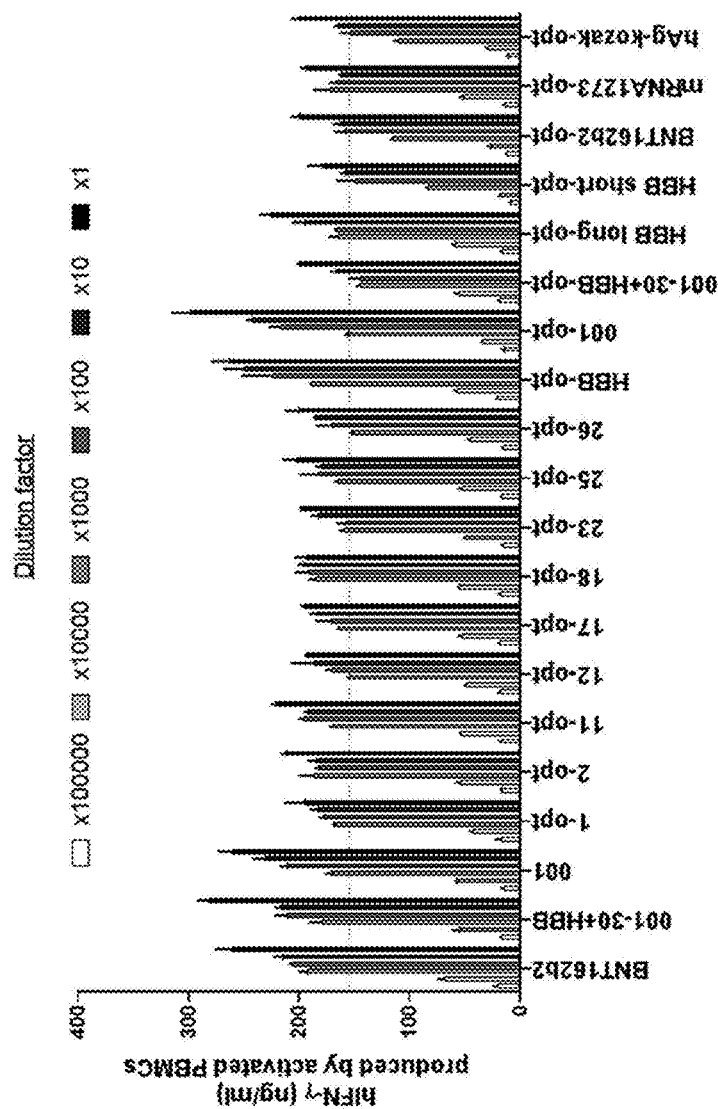
FIG. 5 Comparison of IFN-γ production by human PBMCs stimulated with culture supernatants of scIL-12 mRNA-transfected HeLa cells.

As shown in FIG. 5, consistent with the result of translation efficiency of human scIL-12 mRNA containing various 5'UTR sequences as shown in FIG. 3, the culture supernatants of HeLa cells transfected with scIL-12 mRNA with 5'UTR sequence 001-opt, HBB short-opt, BNT162b2-opt, or hAg Kozak-opt have 0.5-fold lower EC50 of dilution factor than that of HeLa cells transfected with scIL-12 mRNA containing the 5'UTR sequence of BNT162b2, suggesting that the level of translation efficiency of mRNA directly correlates with the biological activity of this mRNA through its resultant proteins.

The invention claimed is:

1. An isolated nucleic acid comprising, in the 5' to 3' direction:
   a) at least one 5'UTR element, said 5'UTR element comprising polynucleotides comprising SEQ ID NO: 38; and
   b) at least one open reading frame (ORF) encoding a peptide or protein.

2. The isolated nucleic acid of claim 1, wherein the isolated nucleic acid further comprises a 3'UTR element and a polyA sequence.

3. The isolated nucleic acid of claim 2, wherein the 3'UTR element comprises SEQ ID NO: 87.

4. The isolated nucleic acid of claim 3, wherein the peptide or protein is a pharmaceutically active protein selected from the group consisting of cytokines; adhesion molecules; immunoglobulins; immunologically active compounds; hormones; growth factors; enzymes; receptors; protease inhibitors; apoptosis regulators; transcription factors; tumor suppressor proteins; structural proteins; reprogramming factors; genomic engineering proteins; and blood proteins.

5. The isolated nucleic acid of claim 4, wherein the peptide or protein is human IL-12 (hIL12).

6. The isolated nucleic acid of claim 4, wherein the peptide or protein comprises one or more antigens of human papillomavirus (HPV).

7. The isolated nucleic acid of claim 1, wherein said isolated nucleic acid comprises SEQ ID NO: 68 or SEQ ID NO: 86.

8. The isolated nucleic acid of claim 1, wherein the ORF is a HPV coding sequence comprising SEQ ID NO: 85.

9. An mRNA comprising, in the 5' to 3' direction:
   a) at least one 5'UTR element, said 5'UTR element comprising polynucleotides comprising SEQ ID NO: 38; and
   b) at least one open reading frame (ORF) encoding a peptide or protein.

10. The mRNA of claim 9, wherein the mRNA further comprises a 3'UTR element and a polyA sequence.

11. The mRNA of claim 10, wherein the 3'UTR element comprises SEQ ID NO: 87.

12. The mRNA of claim 9, wherein the mRNA comprises SEQ ID NO: 68 or SEQ ID NO: 86.

13. The mRNA of claim 9, wherein the mRNA comprises at least one modified or non-naturally occurring nucleotide, wherein the at least one modified or non-naturally occurring nucleotide comprises at least one backbone modification, sugar modification, or base modification.

14. The mRNA of claim 13, wherein the at least one modified or non-naturally occurring nucleotide comprises at least one base modification,
   where the at least one base modification is selected from the group consisting of: 2-amino-6-chloropurine riboside 5' triphosphate, 2-aminoadenosine 5' triphosphate, 2-thiocytidine 5' triphosphate, 2-thiouridine 5' triphosphate, 4-thiouridine 5' triphosphate, 5-aminoallylcytidine 5' triphosphate, 5-aminoallyluridine 5' triphosphate, 5-bromocytidine 5' triphosphate, 5-bromouridine 5' triphosphate, 5-iodocytidine 5' triphosphate, 5-iodouridine 5' triphosphate, 5-methylcytidine 5' triphosphate, 5-methyluridine 5' triphosphate, 6-azacytidine 5' triphosphate, 6-azauridine 5' triphosphate, 6-chloropurine riboside 5'-triphosphate, 7-deazaadenosine 5' triphosphate, 7-deazaguanosine 5' triphosphate, 8-azaadenosine 5' triphosphate, 8-azidoadenosine 5' triphosphate, benzimidazole riboside 5' triphosphate, N1-methyladenosine 5' triphosphate, $N^1$-methylguanosine 5' triphosphate, N6-methyladenosine 5' triphosphate, $O^6$-methylguanosine 5' triphosphate, $N^1$-methyl-pseudouridine 5' triphosphate, puromycin 5'-triphosphate, xanthosine 5' triphosphate, and pseudouridine 5'triphosphate.

15. The mRNA of claim 9, wherein the peptide or protein is a pharmaceutically active protein selected from the group consisting of cytokines; adhesion molecules; immunoglobulins; immunologically active compounds; hormones; growth factors; enzymes; receptors; protease inhibitors; apoptosis regulators; transcription factors; tumor suppressor proteins; reprogramming factors; genomic engineering proteins; and blood proteins.

16. The mRNA of claim 9, wherein the ORF comprises a hIL12 coding sequence comprising SEQ ID NO: 69 or SEQ ID NO: 65 or an HPV coding sequence comprising SEQ ID NO: 85.

17. A pharmaceutical composition comprising the mRNA of claim 9, and one or more excipients.

18. A method for treating or preventing a disorder comprising administering the pharmaceutical composition of claim 17 to a subject in need thereof.

19. The method of claim 18, wherein the disorder is selected from the group consisting of: precancerous lesions, cancer, infectious diseases, condylomata acuminate, HPV infection or HPV infection related diseases or conditions, anemia, diabetes, congenital lung disease, asthma, myocardial infarction, melanoma, autoimmune diabetes, autoimmune myocarditis, inflammation, factor VII deficiency, hemophilia A, hemophilia B, factor X deficiency, factor XI deficiency, factor XIII deficiency, von Willebrand disease, protein C deficiency, antithrombin deficiency, fibrinogen deficiency, hereditary angioedema, al-PI deficiency, Gaucher disease, mucopolysaccharidosis I, mucopolysaccharidosis II, mucopolysaccharidosis VI, mucopolysaccharidosis IVA, mucopolysaccharidosis IIIA, Fabry disease, Pompe disease, Niemann-Pick type B disease, alpha-mannosidosis, metachromatic leukodystrophy, LAL deficiency, sucraseisomaltase deficiency, ADA deficiency, primary IGF-1 deficiency, hypophosphatasia, acute intermittent *porphyria*, X-linked severe combined immunodeficiency (X-SCID), Xeroderma pigmentosum, and immune disorders.

20. The method of claim 18, wherein the subject is a human patient.

* * * * *

SEQUENCE LISTING

```
Sequence total quantity: 87
SEQ ID NO: 1            moltype = DNA  length = 39
FEATURE                 Location/Qualifiers
source                  1..39
                        mol_type = other DNA
                        organism = synthetic construct
SEQUENCE: 1
agggaaataa gaagagtaag aagaaatata agagccacc                          39

SEQ ID NO: 2            moltype = DNA  length = 73
FEATURE                 Location/Qualifiers
source                  1..73
                        mol_type = other DNA
                        organism = synthetic construct
```

-continued

```
SEQUENCE: 2
agggcagcca ctttgcactg gaacttacaa cacccgagca aggacgcgac tctgaagaaa    60
tataagagcc acc                                                       73

SEQ ID NO: 3              moltype = DNA   length = 64
FEATURE                   Location/Qualifiers
source                    1..64
                          mol_type = other DNA
                          organism = synthetic construct
SEQUENCE: 3
agggaaaata taaacataaa cataaacgag atatcacggc cgtggtggac ggataatagc    60
cacc                                                                 64

SEQ ID NO: 4              moltype = DNA   length = 71
FEATURE                   Location/Qualifiers
source                    1..71
                          mol_type = other DNA
                          organism = synthetic construct
SEQUENCE: 4
agggaaaata taaacataaa cataaacgac aagaaacaca tacaaaagaa acaggacaga    60
aaacagccac c                                                         71

SEQ ID NO: 5              moltype = DNA   length = 71
FEATURE                   Location/Qualifiers
source                    1..71
                          mol_type = other DNA
                          organism = synthetic construct
SEQUENCE: 5
agggaaaata taaacataaa cataaacgac aagaaacaca tacaaaagaa acaggacaga    60
aaatagccac c                                                         71

SEQ ID NO: 6              moltype = DNA   length = 71
FEATURE                   Location/Qualifiers
source                    1..71
                          mol_type = other DNA
                          organism = synthetic construct
SEQUENCE: 6
aggaaaaata cacacacaca cacacacaca cacacaaaca cacacacaca cacacaaaca    60
caagagccac c                                                         71

SEQ ID NO: 7              moltype = DNA   length = 71
FEATURE                   Location/Qualifiers
source                    1..71
                          mol_type = other DNA
                          organism = synthetic construct
SEQUENCE: 7
aggaaatata gaaagagaga aagaaagaaa gagagagaga aagagagaaa gaaagaaaga    60
gcagcgccac c                                                         71

SEQ ID NO: 8              moltype = DNA   length = 71
FEATURE                   Location/Qualifiers
source                    1..71
                          mol_type = other DNA
                          organism = synthetic construct
SEQUENCE: 8
aggaataata gagagagaga aagagagaga gagagaaaga gagagagaga gagagagaga    60
gctacgccac c                                                         71

SEQ ID NO: 9              moltype = DNA   length = 80
FEATURE                   Location/Qualifiers
source                    1..80
                          mol_type = other DNA
                          organism = synthetic construct
SEQUENCE: 9
aggaaataca taaacataga aagagaaaac ataacacaca acaaacacat acaacacaaa    60
cacaacacaa actcgccacc                                                80

SEQ ID NO: 10             moltype = DNA   length = 71
FEATURE                   Location/Qualifiers
source                    1..71
                          mol_type = other DNA
                          organism = synthetic construct
SEQUENCE: 10
aggaaaaata ataacatat catactacac aactaacaca tacatcacat acacatcaca    60
taaatgccac c                                                         71
```

| | | |
|---|---|---|
| SEQ ID NO: 11 | moltype = DNA   length = 79 | |
| FEATURE | Location/Qualifiers | |
| source | 1..79<br>mol_type = other DNA<br>organism = synthetic construct | |

SEQUENCE: 11
```
aggcaatact caaatcaat catcatcaca acatcaacaa tcaatcatca acacatcatc   60
agagagagaa gacaccacc                                               79
```

| | | |
|---|---|---|
| SEQ ID NO: 12 | moltype = DNA   length = 68 | |
| FEATURE | Location/Qualifiers | |
| source | 1..68<br>mol_type = other DNA<br>organism = synthetic construct | |

SEQUENCE: 12
```
agggataata ctataactct catctcaaca ctcctcctca ttccaatctc tcacacataa   60
tagccacc                                                           68
```

| | | |
|---|---|---|
| SEQ ID NO: 13 | moltype = DNA   length = 71 | |
| FEATURE | Location/Qualifiers | |
| source | 1..71<br>mol_type = other DNA<br>organism = synthetic construct | |

SEQUENCE: 13
```
agggaaaata taaacataaa cataataaaa cgacaagaaa cacatacaaa agaaaacaga   60
aaacagccac c                                                       71
```

| | | |
|---|---|---|
| SEQ ID NO: 14 | moltype = DNA   length = 73 | |
| FEATURE | Location/Qualifiers | |
| source | 1..73<br>mol_type = other DNA<br>organism = synthetic construct | |

SEQUENCE: 14
```
agggcagcca ctaataacaa aaataaccaa catttaataa aggacgcgaa atagaagaaa   60
tataagagcc acc                                                     73
```

| | | |
|---|---|---|
| SEQ ID NO: 15 | moltype = DNA   length = 73 | |
| FEATURE | Location/Qualifiers | |
| source | 1..73<br>mol_type = other DNA<br>organism = synthetic construct | |

SEQUENCE: 15
```
agggaaaata ctaataacaa aaataaccaa catttaataa attacatgaa atagaagaaa   60
tataagagcc acc                                                     73
```

| | | |
|---|---|---|
| SEQ ID NO: 16 | moltype = DNA   length = 73 | |
| FEATURE | Location/Qualifiers | |
| source | 1..73<br>mol_type = other DNA<br>organism = synthetic construct | |

SEQUENCE: 16
```
agggaataca ctaataacaa aaataaccaa catttaataa aaaacgtgaa atagaagaaa   60
tataagagcc acc                                                     73
```

| | | |
|---|---|---|
| SEQ ID NO: 17 | moltype = DNA   length = 72 | |
| FEATURE | Location/Qualifiers | |
| source | 1..72<br>mol_type = other DNA<br>organism = synthetic construct | |

SEQUENCE: 17
```
agggaaaata taaacataat gtaaagatag aaaaaaattg agaagttaac cgaaaaatag   60
ataatagcca cc                                                      72
```

| | | |
|---|---|---|
| SEQ ID NO: 18 | moltype = DNA   length = 74 | |
| FEATURE | Location/Qualifiers | |
| source | 1..74<br>mol_type = other DNA<br>organism = synthetic construct | |

SEQUENCE: 18
```
agggaaaata taaacacaca cacacataat gtaaagatag aaaaaaattg agaagccgga   60
agataatagc cacc                                                    74
```

```
SEQ ID NO: 19              moltype = DNA   length = 77
FEATURE                    Location/Qualifiers
source                     1..77
                           mol_type = other DNA
                           organism = synthetic construct
SEQUENCE: 19
aggaaaaata cacacacaca gagagaaaga gagaaacaca caaagagaga cacacacaca   60
caaacacaag agccacc                                                 77

SEQ ID NO: 20              moltype = DNA   length = 75
FEATURE                    Location/Qualifiers
source                     1..75
                           mol_type = other DNA
                           organism = synthetic construct
SEQUENCE: 20
agggaaaata taaacacaca acataaacat aaaagaaaca catacaaaag aaagagagaa   60
cagaaaatag ccacc                                                   75

SEQ ID NO: 21              moltype = DNA   length = 79
FEATURE                    Location/Qualifiers
source                     1..79
                           mol_type = other DNA
                           organism = synthetic construct
SEQUENCE: 21
aggaaatata gcacacaaaa aagagagaaa gaaagaaaca cacagagaaa gcacaaaaga   60
aagaaagagc agcgccacc                                               79

SEQ ID NO: 22              moltype = DNA   length = 66
FEATURE                    Location/Qualifiers
source                     1..66
                           mol_type = other DNA
                           organism = synthetic construct
SEQUENCE: 22
aggaataata cacacagaga gaaaagtaag aagagaaaga gagagaagta agaaataaac   60
gccacc                                                             66

SEQ ID NO: 23              moltype = DNA   length = 77
FEATURE                    Location/Qualifiers
source                     1..77
                           mol_type = other DNA
                           organism = synthetic construct
SEQUENCE: 23
aggaaataca tacacacaat taaattctga attcaataac aaacacatat cattaagaca   60
aaagttaact cgccacc                                                 77

SEQ ID NO: 24              moltype = DNA   length = 75
FEATURE                    Location/Qualifiers
source                     1..75
                           mol_type = other DNA
                           organism = synthetic construct
SEQUENCE: 24
aggaaaaata ataacataat cagagagaga gagagagaga aataagagat acatcgagaa   60
aacataaatg ccacc                                                   75

SEQ ID NO: 25              moltype = DNA   length = 78
FEATURE                    Location/Qualifiers
source                     1..78
                           mol_type = other DNA
                           organism = synthetic construct
SEQUENCE: 25
aggcaatact caaaatcata aacataaacg acaacaacaa tcaatcataa taaataaata   60
gagagagaag acaccacc                                                78

SEQ ID NO: 26              moltype = DNA   length = 63
FEATURE                    Location/Qualifiers
source                     1..63
                           mol_type = other DNA
                           organism = synthetic construct
SEQUENCE: 26
agggataata ctataacgag acacacaaac aacaaaaaaa gcgcgccaca cataatagcc   60
acc                                                                63
```

-continued

```
SEQ ID NO: 27           moltype = DNA  length = 66
FEATURE                 Location/Qualifiers
source                  1..66
                        mol_type = other DNA
                        organism = synthetic construct
SEQUENCE: 27
agggaaataa gagagaaaag aagagtaaga agaaatataa gagccaccat ggccaccatg   60
gccacc                                                             66

SEQ ID NO: 28           moltype = DNA  length = 72
FEATURE                 Location/Qualifiers
source                  1..72
                        mol_type = other DNA
                        organism = synthetic construct
SEQUENCE: 28
agggcagagc catctattgc ttacatttgc ttctgacaca actgtgttca ctagcaacct   60
caaacagaca cc                                                      72

SEQ ID NO: 29           moltype = DNA  length = 52
FEATURE                 Location/Qualifiers
source                  1..52
                        mol_type = other DNA
                        organism = synthetic construct
SEQUENCE: 29
agacatttgc ttctgacaca actgtgttca ctagcaacct caaacagaca cc           52

SEQ ID NO: 30           moltype = DNA  length = 104
FEATURE                 Location/Qualifiers
source                  1..104
                        mol_type = other DNA
                        organism = synthetic construct
SEQUENCE: 30
agggaaataa gagagaaaag aagagtaaga acagggcaga gccatctatt gcttacattt   60
gcttctgaca caactgtgtt cactagcaac ctcaaacaga cacc                   104

SEQ ID NO: 31           moltype = DNA  length = 15
FEATURE                 Location/Qualifiers
source                  1..15
                        mol_type = other DNA
                        organism = synthetic construct
SEQUENCE: 31
agggagactg ccacc                                                   15

SEQ ID NO: 32           moltype = DNA  length = 33
FEATURE                 Location/Qualifiers
source                  1..33
                        mol_type = other DNA
                        organism = synthetic construct
SEQUENCE: 32
agggagactg ccaccatggc caccatggcc acc                               33

SEQ ID NO: 33           moltype = DNA  length = 15
FEATURE                 Location/Qualifiers
source                  1..15
                        mol_type = other DNA
                        organism = synthetic construct
SEQUENCE: 33
agggagactg ccaag                                                   15

SEQ ID NO: 34           moltype = DNA  length = 33
FEATURE                 Location/Qualifiers
source                  1..33
                        mol_type = other DNA
                        organism = synthetic construct
SEQUENCE: 34
agggagactg ccaagatggc caagatggcc aag                               33

SEQ ID NO: 35           moltype = DNA  length = 63
FEATURE                 Location/Qualifiers
source                  1..63
                        mol_type = other DNA
                        organism = synthetic construct
SEQUENCE: 35
agggcccaag ctggctagcg gggcgctgcc tacggaggtg gcagccatct ccttctcggc   60
atc                                                                63
```

```
SEQ ID NO: 36            moltype = DNA  length = 63
FEATURE                  Location/Qualifiers
source                   1..63
                         mol_type = other DNA
                         organism = synthetic construct
SEQUENCE: 36
agggcccaag ctggctagcg gggcgctgcc tacggaggtg gcagccatct ccttctcggc    60
acc                                                                 63

SEQ ID NO: 37            moltype = DNA  length = 69
FEATURE                  Location/Qualifiers
source                   1..69
                         mol_type = other DNA
                         organism = synthetic construct
SEQUENCE: 37
agggcccaag ctggctagcg gggcgctgcc tacggaggtg gcagccatct ccttctcggc    60
atcggcacc                                                           69

SEQ ID NO: 38            moltype = DNA  length = 54
FEATURE                  Location/Qualifiers
source                   1..54
                         mol_type = other DNA
                         organism = synthetic construct
SEQUENCE: 38
aggtgtattt actagtaacg taacagtgtt acgtagtgac gtttaactga gact          54

SEQ ID NO: 39            moltype = DNA  length = 54
FEATURE                  Location/Qualifiers
source                   1..54
                         mol_type = other DNA
                         organism = synthetic construct
SEQUENCE: 39
aggtgtattt actagtaacg taacagtgtt acgtagtgac gtttaactga cacc          54

SEQ ID NO: 40            moltype = DNA  length = 48
FEATURE                  Location/Qualifiers
source                   1..48
                         mol_type = other DNA
                         organism = synthetic construct
SEQUENCE: 40
agagtagtaa cagtgtatcg aatcgcaatg aatcatatga gtgacgaa                 48

SEQ ID NO: 41            moltype = DNA  length = 49
FEATURE                  Location/Qualifiers
source                   1..49
                         mol_type = other DNA
                         organism = synthetic construct
SEQUENCE: 41
aggagtagta acagtgtatc gaatcgcaat gaatcatatg agtgacacc                49

SEQ ID NO: 42            moltype = DNA  length = 55
FEATURE                  Location/Qualifiers
source                   1..55
                         mol_type = other DNA
                         organism = synthetic construct
SEQUENCE: 42
aggagtagta acagtgtatc gaatcgcaat gaatcatatg agtgacgaag ccacc         55

SEQ ID NO: 43            moltype = DNA  length = 72
FEATURE                  Location/Qualifiers
source                   1..72
                         mol_type = other DNA
                         organism = synthetic construct
SEQUENCE: 43
aggtaacgta attgcatacc gtgaatatcg tagtgaactg agtagtaaac cgtttgttaa    60
ttaatgagca gt                                                       72

SEQ ID NO: 44            moltype = DNA  length = 72
FEATURE                  Location/Qualifiers
source                   1..72
                         mol_type = other DNA
                         organism = synthetic construct
SEQUENCE: 44
aggtaacgta attgcatacc gtgaatatcg tagtgaactg agtagtaaac cgtttgttaa    60
ttaatagaca cc                                                       72
```

-continued

```
SEQ ID NO: 45          moltype = DNA   length = 78
FEATURE                Location/Qualifiers
source                 1..78
                       mol_type = other DNA
                       organism = synthetic construct
SEQUENCE: 45
aggtaacgta attgcatacc gtgaatatcg tagtgaactg agtagtaaac cgtttgttaa    60
ttaatgagca gtgacacc                                                 78

SEQ ID NO: 46          moltype = DNA   length = 74
FEATURE                Location/Qualifiers
source                 1..74
                       mol_type = other DNA
                       organism = synthetic construct
SEQUENCE: 46
aggtattacg taacctgttg aattcgtact tgatagctaa tctaaaaatg aacagtctga    60
atatgatcgg aaac                                                     74

SEQ ID NO: 47          moltype = DNA   length = 74
FEATURE                Location/Qualifiers
source                 1..74
                       mol_type = other DNA
                       organism = synthetic construct
SEQUENCE: 47
aggtattacg taacctgttg aattcgtact tgatagctaa tctaaaagtg aacagtctga    60
atataatcga cacc                                                     74

SEQ ID NO: 48          moltype = DNA   length = 80
FEATURE                Location/Qualifiers
source                 1..80
                       mol_type = other DNA
                       organism = synthetic construct
SEQUENCE: 48
aggtattacg taacctgttg aattcgtact tgatagctaa tctaaaaatg aacagtctga    60
atatgatcgg aaacggcacc                                               80

SEQ ID NO: 49          moltype = DNA   length = 42
FEATURE                Location/Qualifiers
source                 1..42
                       mol_type = other DNA
                       organism = synthetic construct
SEQUENCE: 49
attcttctgg tccccacaga ctctcagaga gaacccgcca cc                      42

SEQ ID NO: 50          moltype = DNA   length = 39
FEATURE                Location/Qualifiers
source                 1..39
                       mol_type = other DNA
                       organism = synthetic construct
SEQUENCE: 50
agcgttatga atcgcgtaat ggacgttatg agcgcagac                          39

SEQ ID NO: 51          moltype = DNA   length = 73
FEATURE                Location/Qualifiers
source                 1..73
                       mol_type = other DNA
                       organism = synthetic construct
SEQUENCE: 51
agtagagcta gttaacattg tgaattactt aacgtttgct aacatgaaca tgctagcgaa    60
tatgagcgtg aag                                                      73

SEQ ID NO: 52          moltype = DNA   length = 79
FEATURE                Location/Qualifiers
source                 1..79
                       mol_type = other DNA
                       organism = synthetic construct
SEQUENCE: 52
aggcgttatt cgtagttagt gaatagcgta tcagttactg ttaatcgtta acagtttaat    60
agcgttagtg actagtgca                                                79

SEQ ID NO: 53          moltype = DNA   length = 68
FEATURE                Location/Qualifiers
source                 1..68
                       mol_type = other DNA
                       organism = synthetic construct
SEQUENCE: 53
agcgtgaact gttaaaccgt tatttgaatc gcgttatgca ttccaatatg aatcgcgtaa    60
tgtctact                                                            68
```

```
SEQ ID NO: 54          moltype = DNA   length = 77
FEATURE                Location/Qualifiers
source                 1..77
                       mol_type = other DNA
                       organism = synthetic construct
SEQUENCE: 54
agcgcagtcg tatacgcgtt aacgtagtgt atttagtgac taacgcattt cgttaatagt   60
aacgttaact agtgaag                                                  77

SEQ ID NO: 55          moltype = DNA   length = 78
FEATURE                Location/Qualifiers
source                 1..78
                       mol_type = other DNA
                       organism = synthetic construct
SEQUENCE: 55
aggcgttatt taacgtagtg agcgttaacg ttaacagtga acagtctgat ttccgtaatg   60
gatcgcgtag ttagcatg                                                 78

SEQ ID NO: 56          moltype = DNA   length = 63
FEATURE                Location/Qualifiers
source                 1..63
                       mol_type = other DNA
                       organism = synthetic construct
SEQUENCE: 56
agggatcaca gcgtaacgtt cgtgacgaat ttcgtaaccg acatgcatcg tttaatggat   60
act                                                                 63

SEQ ID NO: 57          moltype = DNA   length = 72
FEATURE                Location/Qualifiers
source                 1..72
                       mol_type = other DNA
                       organism = synthetic construct
SEQUENCE: 57
agcgtatatc cgtttatagc gtacttgatc gttttaatga cgttcgcaaa catgaatcgc   60
gtaattaaaa tg                                                       72

SEQ ID NO: 58          moltype = DNA   length = 52
FEATURE                Location/Qualifiers
source                 1..52
                       mol_type = other DNA
                       organism = synthetic construct
SEQUENCE: 58
agtcgtttac tagtagcgta tacgttttaa ttagtgacgt ttaactgaga ct           52

SEQ ID NO: 59          moltype = DNA   length = 104
FEATURE                Location/Qualifiers
source                 1..104
                       mol_type = other DNA
                       organism = synthetic construct
SEQUENCE: 59
agggtcgtaa gccggtaacg taacgtagtg agacggaata gtaacgtatt gattacgttt   60
actagtagcg tatcgtgtt aattagtgac gttaactaga cgaa                    104

SEQ ID NO: 60          moltype = DNA   length = 53
FEATURE                Location/Qualifiers
source                 1..53
                       mol_type = other DNA
                       organism = synthetic construct
SEQUENCE: 60
agtcgttact agtgaacttc cgtttaaccg tgaatatgaa tctgatcgga gac           53

SEQ ID NO: 61          moltype = DNA   length = 58
FEATURE                Location/Qualifiers
source                 1..58
                       mol_type = other DNA
                       organism = synthetic construct
SEQUENCE: 61
aggttaataa cagtgaatcg cagtgtgata aaatcgttag tgaatgtccg ttaataga     58

SEQ ID NO: 62          moltype = DNA   length = 44
FEATURE                Location/Qualifiers
source                 1..44
                       mol_type = other DNA
                       organism = synthetic construct
SEQUENCE: 62
agttcgttat gagcgtaaac atgaatatga acgttatcgg aagt                    44
```

| | | |
|---|---|---|
| SEQ ID NO: 63 | moltype = DNA length = 39 | |
| FEATURE | Location/Qualifiers | |
| source | 1..39 | |
| | mol_type = other DNA | |
| | organism = synthetic construct | |
| SEQUENCE: 63 | | |
| agggtcttct ggtccccaca gactcagaga gaacccacc | | 39 |

| | | |
|---|---|---|
| SEQ ID NO: 64 | moltype = DNA length = 48 | |
| FEATURE | Location/Qualifiers | |
| source | 1..48 | |
| | mol_type = other DNA | |
| | organism = synthetic construct | |
| SEQUENCE: 64 | | |
| agggaaataa gagagaaaag aagagtaaga agaaatataa gagccacc | | 48 |

| | | |
|---|---|---|
| SEQ ID NO: 65 | moltype = DNA length = 1620 | |
| FEATURE | Location/Qualifiers | |
| source | 1..1620 | |
| | mol_type = other DNA | |
| | organism = Homo sapiens | |

SEQUENCE: 65

```
atgtgtcacc agcagttggt catctcttgg ttttccctgg ttttttctggc atctcccctc    60
gtggccatat gggaactgaa gaaagatgtt tatgtcgtag aattggattg gtatccggat   120
gcccctggag aaatggtggt cctcacctgt gacacccctg aagaagatgg tatcacctgg   180
accttggacc agagcagtga ggtcttaggc tctggcaaaa ccctgaccat ccaagtcaaa   240
gagtttggag atgctggcca gtacacctgt cacaaaggag gcgaggttct aagccattcg   300
ctcctgctgc ttcacaaaaa ggaagatgga atttggtcca ctgatatttt aaaggaccag   360
aaagaaccca aaaataagac cttttctaaga tgcgaggcca agaattattc tggacgtttc   420
acctgctggt ggctgacgac aatcagtact gatttgacat tcagtgtcaa aagcagcaga   480
ggcagctctg accccaagg ggtgacgtgc ggagctgcta cactctctgc agagagagtc    540
agaggggaca caaggagta tgagtactca gtggagtgcc aggaggacag tgcctgccca   600
gctgctgagg agagtctgcc cattgaggtc atggtggatg ccgttcacaa gctcaagtat   660
gaaaactaca ccagcagctt cttcatcagg gacatcatca acctgacca acccaagaac   720
ttgcagctga agccattaaa gaattctcgg caggtggagg tcagctggga gtaccctgac   780
acctggagta ctccacattc ctacttctct ctgacattct gcgttcaggt ccagggcaag   840
agcaagagag aaaagaaaga tagagtcttc acggacaaga cctcagccac ggtcatctgc   900
cgcaaaaatg ccagcattag cgtgcgggcc caggaccgct actatagctc atcttggagc   960
gaatgctgca ctgtgccctg cagtggtggc ggagggagcg gtggcggagg gagcggttgc  1020
ggagggagca gaaacctccc cgtggccact ccagacccag aatgttccc atgccttcac  1080
cactcccaaa acctgctgag ggccgtcagc aacatgctcc agaaggccag acaaactcta  1140
gaatttttacc cttgcacttc tgaagagatt gatcatgaag atatcacaaa agataaaacc  1200
agcacagtgg aggcctgttt accattggaa ttaaccagaa atgagagttg cctaaattcc  1260
agagagacct cttttcataac taatgggagt tgcctggcct ccagaaagac ctcttttatg  1320
atggccctgt gccttagtag tatttatgaa gacttgaaga tgtaccaggt gggagttcaag  1380
accatgaatg caaagcttct gatggatcct aagaggcaga tctttctaga tcaaaacatg  1440
ctggcagtta ttgatgagct gatgcaggcc ctgaatttca acagtgagc tgtgccacaa  1500
aaatcctccc ttgaagaacc ggattttttat aaaactaaaa tcaagctctg catactttcttt  1560
catgctttca gaattcgggc agtgactatt gatagagtga tgagctatct gaatgcttcc  1620
```

| | | |
|---|---|---|
| SEQ ID NO: 66 | moltype = DNA length = 52 | |
| FEATURE | Location/Qualifiers | |
| source | 1..52 | |
| | mol_type = other DNA | |
| | organism = synthetic construct | |
| SEQUENCE: 66 | | |
| gggcgaacta gtattcttct ggtccccaca gactcagaga gaacccgcca cc | | 52 |

| | | |
|---|---|---|
| SEQ ID NO: 67 | moltype = DNA length = 47 | |
| FEATURE | Location/Qualifiers | |
| source | 1..47 | |
| | mol_type = other DNA | |
| | organism = synthetic construct | |
| SEQUENCE: 67 | | |
| gggaaataag agagaaaaga agagtaagaa gaaatataag agccacc | | 47 |

| | | |
|---|---|---|
| SEQ ID NO: 68 | moltype = DNA length = 1927 | |
| FEATURE | Location/Qualifiers | |
| source | 1..1927 | |
| | mol_type = other DNA | |
| | organism = synthetic construct | |

SEQUENCE: 68

```
aggtgtattt actagtaacg taacagtgtt acgtagtgac gtttaactga gactatgggc    60
gtgaaggtcc tgttcgccct catttgcatt gctgtggccg aggcatctg ggaactgggc   120
aaggatgtgt acgtggtgga gctcgactgg tatcctgatg cccgggagga aatggtggtg   180
ctgacgtgcg acaccccga agaggatggt atcacctgga cccctggatca gtcatccgaa   240
gtgctgggct cggggaaaac tctgaccatc caagtcaaag agtttggcga cgccggacag   300
tacacctgtc acaaggcgg agaggtgctc agccattcgc tgctcctcct gcataagaag   360
gaggacggca tctggtccac cgacattttg aaagaccaga aggagcccaa gaacaagacc   420
```

```
ttcctgagat gcgaagctaa gaattactcc ggccggttca cttgttggtg gctgaccacc   480
atctccactg acctgacctt ctcggtgaaa agctcaaggg ggtcgagcga tccgcagggc   540
gtgacttgtg gagcagcgac gcttagcgcc gaaagggtcc gcggcgacaa caaggagtac   600
gagtactccg tggaatgcca ggaggatagc gcatgtccgg ctgcgaaga gtcgctgccg    660
attgaagtca tggtcgatgc cgtgcacaag ctgaaatacc aaaactacac ctcatccttc   720
tttatccggg acatcattaa gcctgatcct cccaagaatc tgcagctcaa gcccttaag   780
aacagccgcc aagtggaagt gtcctgggaa tacccggata cctggtccac cccgcactcc   840
tacttctcct tgactttctg cgtccaagtg cagggaaagt ccaagcggga gaagaaggac   900
cgggtgttca ctgacaagac atccgcgacc gtgatctgcc gcaagaatgc gtccatatca   960
gtgcgcgccc aggacagata ctactcctcc tcctggtccg aatgggcctc agtcccatgc  1020
tccgggggat cggccggtgg aagcgccggt ggttcgcccg gaggatccaa gcgcaacctt  1080
ccggtggcca ctcctgaccc gggaatgttc ccatgtctgc accactccca aaaccttctg  1140
agagcagtct caaacatgct gcagaaggcc cggcagactc tggaattcta ccctgcacc   1200
tcggaggaaa tcgatcacga ggacattact aaggacaaga cctctaccgt ggaggcctgc  1260
ctgcctctcg agctgaccaa gaacgagagc tgcctgaaca gcagggaaac ctcctttatc  1320
accaacggaa gctgcctggc cagcagaaag acttccttca tgatggccct gtgcctgagc  1380
agcatctacg aggacctcaa gatgtatcag gtcgagttca agactatgaa cgccaagctt  1440
ctgatgacc ccaagcggca gattttcctg gaccagaaca tgctggcgt gattgacgaa  1500
ctgatgcagg ccctgaactt caactccgaa accgtgcccc aaaagtcgag cctggaggag  1560
ccagacttct acaagaccaa gatcaagctc tgcatcctgc tgcatgcgtt ccggatccgg  1620
gctgtgacaa ttgaccgcgt gatgtcctac ctcaacgcct cctgataata ggctcgcttt  1680
cttgctgtcc aatttctatt aaaggttcct ttgttcccta agtccaacta ctaaactggg  1740
ggatattatg aagggccttg agcatctgga ttctgcctaa taaaaaacat ttattttcat  1800
tgcaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaa                                                            1927

SEQ ID NO: 69           moltype = DNA  length = 1566
FEATURE                 Location/Qualifiers
source                  1..1566
                        mol_type = other DNA
                        organism = synthetic construct
SEQUENCE: 69
atctgggaac tgaagaagga tgtgtacgtg gtggagctcg actggtatcc tgatgccccg    60
ggagaaatgg tggtgctgac gtgcgacacc cccgaagagg atggtatcac ctggaccctg   120
gatcagtcat ccgaagtgct gggctcgggg aaaactctga ccatccaagt caaagagttt   180
ggcgacgccg gacagtacac ctgtcacaag gcgagagg tgctcagcca ttcgctgctc    240
ctcctgcata agaaggagga cggcatctgg tccaccgaca tttgaaaga ccagaaggag   300
cccaagaaca agaccttcct gagatgcgaa gctaagaatt actccggccg gttcacttg   360
tggtggctga ccaccatctc cactgacctg accttctcgg tgaaaagctc aaggggtcg    420
agcgatccgc agggcgtgac ttgtggagca gcgacgctta gcgccgaaag ggtccgcggc   480
gacaacaagg agtacgagta ctccgtgaa tgccaggagg atagcgcatg tccggctgcg    540
gaagtcgc tgccgattga agtcatggtc gatgccgtgc acaagctgaa atacgaaaac    600
tacacctcat ccttctttat ccgggacatc attaagcctg atcctcccaa gaatctgcag   660
ctcaagcccc ttaagaacag ccgccaagtg gaagtgtcct gggaatcc ggataccctgg   720
tccaccccgc actcctactt ctccttgact ttctgcgtcc aagtgcaggg aaagtccaag   780
cgggagaaga aggaccgggt gttcactgac aagacatccg cgaccgtgat ctgccgcaag   840
aatgcgtcca tatcagtgcg cgcccaggac agatactact cctcctcctg gtccgaatgg   900
gcctcagtcc catgctccgg gggatcggcc ggtggaagcg ccggtggttc gcccggagga   960
tccaagcgca accttccggt ggccactcct gacccgggaa tgttcccatg tctgcaccac  1020
tcccaaaaac ttctgagagc agtctcaaac atgctgcaga aggcccggca gactctggaa  1080
ttctacccct gcacctcgga ggaaatcgat cacgaggaca ttactaagga caagacctct  1140
accgtggagg cctgcctgcc tctcgagctg accaagaacg agagctgcct gaacagcagg  1200
gaaacctcct ttatcaccaa cggaagctgc ctggccagca gaaagacttc cttcatgatg  1260
gccctgtgcc tgagcagcat ctacgaggac ctcaagatgt atcaggtcga gttcaagact  1320
atgaacgcca agcttctgat ggaccccaag cggcagattt tcctggacca gaacatgctg  1380
gccgtgattg acgaactgat gcaggccctg aacttcaact ccgaaccgt gccccaaaag   1440
tcgagcctgg aggagccaga cttctacaag accaagatca gctctgcat cctgctgcat   1500
gcgttccgga tccgggctgt gacaattgac cgcgtgatgt cctacctcaa cgcctcctga  1560
taatag                                                             1566

SEQ ID NO: 70           moltype = DNA  length = 2099
FEATURE                 Location/Qualifiers
source                  1..2099
                        mol_type = other DNA
                        organism = synthetic construct
SEQUENCE: 70
gggcgaacta gtattcttct ggtccccaca gactcagaga gaacccgcca ccatgtgtca    60
ccagcagctg gtgatctcat ggttctccct ggtatttctg gcatctcctc ttgtcgcaat   120
ctggaactg aagaaagacg tgtatgtcgt tgagctcgac tggtatccgg atgcgcctgg   180
cgagatggtg gtgctgacct gtgacacccc agaggaggat gggatcactt ggaccctga   240
tcaatcctcc gaagtgctcg ggtctggcaa gactctgacc atacaagtga agagtttgg   300
cgatgccggg cagtacactt gccataaggg cggagaagtt ctgtcccact cactgctgct   360
gctgcacaag aaagaggacg gaatttggag tacgatac tgaaagatc agaaaggcc     420
caagaacaaa accttcttgc ggtgcgaagc caagaactac tcaggagat ttacttgttg   480
gtggctgacg acgatcagca ccgatctgac tttctccgtg aaatcaagta ggggatcatc   540
tgaccctcaa ggagtcacat gtggagcggc tactctgagc gctgaacgcg taagagggga   600
caataaggag tacgagtata gcgttgagtg ccaagaggat agcgcatgcc ccgccgcga    660
agaatcattg cccattgaag tgatggtgga tgctgtacac aagctgaagt atgagaacta   720
```

```
cacaagctcc ttcttcatcc gtgacatcat caaaccagat cctcctaaga acctccagct    780
taaacctctg aagaactcta gacaggtgga agtgtcttgg gagtatcccg acacctggtc    840
tacaccacat tcctacttca gtctcacatt ctgcgttcag gtacagggca agtccaaaag    900
ggagaagaag gatcgggtct ttacagataa acaagtgcc accgttatat gccggaagaa     960
tgcctctatt tctgtgcgtg cgcaggacag atactatagc agctcttgga gtgaatgggc   1020
cagtgtccca tgttcagggt catccggtgg tgcggcagc cccggaggcg gtagctccag    1080
aaatctcccc gtggctacac ctgatccagg catgtttccc tgtttgcacc atagccaaaa   1140
cctcctgaga gcagtcagca acatgctcca gaaagctaga caaacactgg aattctaccc   1200
atgcacctcc gaggaaatag atcacgagga tatcactaag gacaaaacaa gcactgtcga   1260
agcatgcctt cccttggaac tgacaaagaa cgagagttgc cttaattcaa gagaaacatc   1320
tttcattaca aacggtagct gcttggcaag cagaaaaaca tcttttatga tggccctttg   1380
tctgagcagt atttatgagg atctcaaaat gtaccaggtg gagtttaaga ccatgaatgc   1440
caagctgctg atggacccaa agagacagat tttcctcgat cagaatatgc tggctgtgat   1500
tgatgaactg atgcaggcct tgaatttcaa cagcgaaacc gttccccaga aaagcagtct   1560
tgaagaacct gacttttata agaccaagat caaactgtgt attctcctgc atgcctttag   1620
aatcagagca gtcactatag atagagtgat gtcctacctg aatgcttcct gatgatagct   1680
cgagagctcg ctttcttgct gtccaatttc tattaaaggt tcctttgttc cctaagtcca   1740
actactaaac tgggggatat tatgaagggc cttgagcatc tggattctgc ctaataaaaa   1800
acatttattt tcattgctgc gtcgagagct cgctttcttg ctgtccaatt tctattaaag   1860
gttcctttgt tccctaagtc caactactaa actgggggat attatgaagg ccttgagca   1920
tctggattct gcctaataaa aaacatttat tttcattgct gcgtcgagac ctggtccaga   1980
gtcgctagca aaaaaaaaa aaaaaaaaa aaaaaaaag catatgacta aaaaaaaaaa     2040
aaaaaaaaaa aaaaaaaaaa aaaaaaaaaa aaaaaaaaaa aaaaaaaaaa aaaaaaaaa    2099

SEQ ID NO: 71           moltype = DNA   length = 1884
FEATURE                 Location/Qualifiers
source                  1..1884
                        mol_type = other DNA
                        organism = synthetic construct
SEQUENCE: 71
gggaaataag agagaaaaga agagtaagaa gaaatataag agccaccatg tgccaccagc     60
agctggtgat cagctggttc agcctggtgt tcctggccag cccccctgtg gccatctggg    120
agctgaagaa ggacgtgtac gtggtggagt tggattggta ccccgacgcc cccggcgaga    180
tggtggtgct gacctgcgac acccccgagg aggacggcat cacctggacc ctggaccaga    240
gcagcgaggt gctgggcagc ggcaagaccc tgaccatccg ggtgaaggag ttcggcgacg    300
ccggccagta cacctgccac aagggcggcg aggtgctgag ccacagcctg ctgctgctgc    360
acaagaagga ggacggcatc tggagcaccg acatcctgaa ggaccagaag gagcccaaga    420
acaagaacctt cctgagatgc gaggccaaga actacagcgg cagattcacc tgctggtggc    480
tgaccaccat cagcaccgac ctgaccttca gcgtgaagag cagcagaggc agcagcgacc    540
cccagggcgt gacctgcggc gccgccaccc tgagcgccga gagtgaga ggcgacaaca    600
aggagtacga gtacagcgtg gagtgccagg aagatagcgc ctgccccgcc gccgaggaga    660
gcctgccat cgaggtgatg gtggacgccg tgcacaagct gaagtacgag aactacacca    720
gcagcttctt catcagagat atcatcaagc ccgaccccc caagaacctg cagctgaagc    780
ccctgaagaa cagccggcag gtggaggtga gctgggagta ccccgacacc tggagcaccc    840
cccacagcta cttcagcctg accttctgcg tgcaggtgca gggcaagagc aagagagaga    900
agaaagatag agtgttcacc gacaagacca gcgccaccgt gatctgcaga aagaacgcca    960
gcatcagcgt gagagcccaa gatagatact acagcagcag ctggagcgag tgggccagcg   1020
tgccctgcag cggcggcggc ggcggcggca gcagaaaccct gcccgtggcc acccccgacc   1080
ccggcatgtt cccctgcctg caccacagcc agaacctgct gagagccgtg agcaacatgc   1140
tgcagaaggc ccggcagacc ctggagttct acccctgcac cagcgaggag atcgaccacg   1200
aagatatcac caagagtaag accagcaccg tggaggcctg cctgcccctg agctgacca   1260
agaacgagag ctgcctgaac agcagagaga ccagcttcat caccaacggc agctgcctgg   1320
ccagcagaaa gaccagcttc atgatggccc tgtgcctgag cagcatctac gaggacctga   1380
agatgtacca ggtggagttc aagaccatga acgccaagct gctgatggac cccaagcggc   1440
agatcttcct ggaccagaac atgctggccg tgatcgacga gctgatgcag gccctgaact   1500
tcaacagcga gaccgtgccc cagaagagca gcctggagga gcccgacttc tacaagacca   1560
agatcaagct gtgcatcctg ctgcacgcct tcagaatcag accgtgacc atcgacagag   1620
tgatgagcta cctgaacgcc agctgataat aggctggagc ctcggtggcc atgcttcttg   1680
cccctgggc ctccccag cccctcctcc ccttcctgca cccgtacccc ccaaacacca    1740
ttgtcacact ccagtggtct ttgaataaag tctgagtggg cggcaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaa                                         1884

SEQ ID NO: 72           moltype = DNA   length = 104
FEATURE                 Location/Qualifiers
source                  1..104
                        mol_type = other DNA
                        organism = synthetic construct
SEQUENCE: 72
agggaaataa gagagaaaag aagagtaaga acagggcaga gccatctatt gcttacattt     60
gcttctgaca caactgtgtt cactagcaac ctcaaacagc cacc                    104
```

```
SEQ ID NO: 73            moltype = DNA   length = 58
FEATURE                  Location/Qualifiers
source                   1..58
                         mol_type = other DNA
                         organism = synthetic construct
SEQUENCE: 73
agggaaataa gagagaaaag aagagtaaga agaaatataa gaccccggcg ccgccacc         58

SEQ ID NO: 74            moltype = DNA   length = 64
FEATURE                  Location/Qualifiers
source                   1..64
                         mol_type = other DNA
                         organism = synthetic construct
SEQUENCE: 74
agggaaataa cagtgaatcg cagtgtgata aaatcgttag tgaatatccg ttaatagagc       60
cacc                                                                    64

SEQ ID NO: 75            moltype = DNA   length = 58
FEATURE                  Location/Qualifiers
source                   1..58
                         mol_type = other DNA
                         organism = synthetic construct
SEQUENCE: 75
aggttaataa cagtgaatcg cagtgtgata aaatcgttag tgaatatccg ttgccacc         58

SEQ ID NO: 76            moltype = DNA   length = 53
FEATURE                  Location/Qualifiers
source                   1..53
                         mol_type = other DNA
                         organism = synthetic construct
SEQUENCE: 76
aggagttact agtgaacttc cgtttaaccg tgaatatgaa tctgatcgga gac              53

SEQ ID NO: 77            moltype = DNA   length = 53
FEATURE                  Location/Qualifiers
source                   1..53
                         mol_type = other DNA
                         organism = synthetic construct
SEQUENCE: 77
aggagttact agtgaacttc cgtttaaccg tgaataggaa tctgatcgcc acc              53

SEQ ID NO: 78            moltype = DNA   length = 54
FEATURE                  Location/Qualifiers
source                   1..54
                         mol_type = other DNA
                         organism = synthetic construct
SEQUENCE: 78
agggacattt gcttctgaca caactgtgtt cactagcaac ctcaaacaga cacc             54

SEQ ID NO: 79            moltype = DNA   length = 54
FEATURE                  Location/Qualifiers
source                   1..54
                         mol_type = other DNA
                         organism = synthetic construct
SEQUENCE: 79
aggtgtattt actagtaacg taacagtgtt acgtagtgac gtttaactgc cacc             54

SEQ ID NO: 80            moltype = DNA   length = 78
FEATURE                  Location/Qualifiers
source                   1..78
                         mol_type = other DNA
                         organism = synthetic construct
SEQUENCE: 80
agggttattc gtagttagtg aatagcgtat cagttactgt taatcgttaa cagtttaata       60
gcgttagtga ctagtgca                                                     78

SEQ ID NO: 81            moltype = DNA   length = 79
FEATURE                  Location/Qualifiers
source                   1..79
                         mol_type = other DNA
                         organism = synthetic construct
SEQUENCE: 81
aggagttatt cgtagttagt gaatagcgta tcagttactg ttaatcgtta acagtttaat       60
agcgttagtg actgccacc                                                    79
```

| SEQ ID NO: 82 | moltype = DNA length = 78 |
| --- | --- |
| FEATURE | Location/Qualifiers |
| source | 1..78 |
| | mol_type = other DNA |
| | organism = synthetic construct |

SEQUENCE: 82
```
agggttattc gtagttagtg aatagcgtat cagttactgt taatcgttaa cagtttaata    60
gcgttagtga ctgccacc                                                  78
```

| SEQ ID NO: 83 | moltype = DNA length = 72 |
| --- | --- |
| FEATURE | Location/Qualifiers |
| source | 1..72 |
| | mol_type = other DNA |
| | organism = synthetic construct |

SEQUENCE: 83
```
aggtaacgta attgcatacc gtgaatatcg tagtgaactg agtagtaaac cgtttgttaa    60
ttaatagcca cc                                                        72
```

| SEQ ID NO: 84 | moltype = DNA length = 74 |
| --- | --- |
| FEATURE | Location/Qualifiers |
| source | 1..74 |
| | mol_type = other DNA |
| | organism = synthetic construct |

SEQUENCE: 84
```
aggtattacg taacctgttg aattcgtact tgatagctaa tctaaaagtg aacagtctga    60
atataatcgc cacc                                                      74
```

| SEQ ID NO: 85 | moltype = DNA length = 792 |
| --- | --- |
| FEATURE | Location/Qualifiers |
| source | 1..792 |
| | mol_type = other DNA |
| | organism = synthetic construct |

SEQUENCE: 85
```
atggactgga cctggatcct gttcctggtg gccgccgcca ccagagtgca cagcttccag    60
gaccccagg agagcggcag aaagctgccc cagctgtgca ccgagctgca gaccaccatc   120
cacgacatca tcctggagtg cgtgtactgc aagcagcagc tgctgagaag agaggtgtac   180
gacagagacc tgtgcatcgt gtacagagac ggcaacccct acgccgtgtg cgacaagtgc   240
ctgaagttct acagcaagat cagcgagtac agacactact gctacagcgt gtacggcacc   300
accctggagc agcagtacaa caagcccctg tgcgacctgc tgatcagatg catcaactgc   360
cagaagcccc tgcagagaca cctggacaag aagcagagat ccacaacat cagaggcaga   420
tggaccggca gatgcatgag ctgctgcaga agcagcagaa ccagaagaga gacccagctg   480
agaggcagaa agagaagaag ccacggcgac accccaccc tgcacgagta catgctggac   540
ctgcagcccg agaccaccga cctgtacggc tacggcagc tgaacgacag cagcgaggag   600
gaggacgaga tcgacggccc cgccggccag gccgagcccg acagagccca ctacaacatc   660
gtgaccttct gctgcaagtg cgacagcacc ctgagactgt gcgtgcagag cacccacgtg   720
gacatcagaa ccctggagga cctgctgatg gcaccctgg catcgtgtg ccccatctgc   780
agccagaagc cc                                                        792
```

| SEQ ID NO: 86 | moltype = DNA length = 1107 |
| --- | --- |
| FEATURE | Location/Qualifiers |
| source | 1..1107 |
| | mol_type = other DNA |
| | organism = synthetic construct |

SEQUENCE: 86
```
aggtgtattt actagtaacg taacagtgtt acgtagtgac gtttaactga gactatggac    60
tggacctgga tcctgttcct ggtggccgcc gccaccagag tgcacagctt ccaggacccc   120
caggagagcg gcagaaagct gccccagctg tgcaccgagc tgcagaccac catccacgac   180
atcatcctgg agtgcgtgta ctgcaagcag cagctgctga agagaggt gtacgacaga   240
gacctgtgca tcgtgtacag agacggcaac ccctacgccg tgtgcgacaa gtgcctgaag   300
ttctacagca agatcagcga gtacagacac tactgctaca gcctgtacgg caccaccctg   360
gagcagcagt acaacaagcc cctgtgcgac ctgctgatca gatgcatcaa ctgccagaag   420
cccctgcaga gacacctgga caagaagcag agattccaca acatcagagg cagatggacc   480
ggcagatgca tgagctgctg cagaagcagc agaaccagaa gagagaccca gctgagaggc   540
agaaagagaa gaagccacgg cgacaccccc accctgcacg agtacatgct ggacctgcag   600
cccgagacca ccgacctgta cggctacggc agctgaacg acagcagcga ggaggaggac   660
gagatcgacg gccccgccgg ccaggccgag cccgacagag cccactacaa catcgtgacc   720
ttctgctgca agtgcgacag caccctgaga ctgtgcgtgc agagcaccca cgtggacatc   780
agaaccctgg aggacctgct gatgggcacc ctgggcatcg tgtgccccat ctgcagccag   840
aagcccgat aataggctcg ctttcttgct gtccaatttc tattaaaggt tcctttgttc   900
cctaagtcca actactaaac tgggggatat atgaagggc cttgagcatc tggattctgc   960
ctaataaaaa acatttattt tcattgcaaa aaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaa                                      1107
```

```
SEQ ID NO: 87         moltype = DNA  length = 132
FEATURE               Location/Qualifiers
source                1..132
                      mol_type = other DNA
                      organism = synthetic construct
SEQUENCE: 87
gctcgctttc ttgctgtcca atttctatta aaggttcctt tgttccctaa gtccaactac    60
taaactgggg gatattatga agggccttga gcatctggat tctgcctaat aaaaaacatt   120
tattttcatt gc                                                       132
```